US011413375B2

(12) United States Patent
Badylak et al.

(10) Patent No.: US 11,413,375 B2
(45) Date of Patent: *Aug. 16, 2022

(54) METHODS FOR PREPARATION OF A TERMINALLY STERILIZED HYDROGEL DERIVED FROM EXTRACELLULAR MATRIX

(71) Applicant: University of Pittsburgh—Of the Commonwealth System of Higher Education, Pittsburgh, PA (US)

(72) Inventors: Stephen F. Badylak, West Lafayette, IN (US); Christopher Lee Dearth, Laytonsville, MD (US); Timothy Joseph Keane, Jr., Wellsboro, PA (US); Neill Jordon Turner, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/238,826

(22) Filed: Jan. 3, 2019

(65) Prior Publication Data

US 2019/0374683 A1 Dec. 12, 2019

Related U.S. Application Data

(63) Continuation of application No. 15/127,707, filed as application No. PCT/US2015/021732 on Mar. 20, 2015, now Pat. No. 10,213,526.

(Continued)

(51) Int. Cl.
*A61L 27/52* (2006.01)
*A61L 27/36* (2006.01)
(Continued)

(52) U.S. Cl.
CPC ............... *A61L 27/52* (2013.01); *A61L 27/36* (2013.01); *A61L 27/3633* (2013.01);
(Continued)

(58) Field of Classification Search
CPC .. A61L 27/3633; A61L 27/48; A61L 27/3687; A61L 31/048; A61L 31/06; A61L 2430/06; A61L 27/52; A61L 27/54; A61L 27/14; A61L 27/3629; A61L 27/50; A61L 27/58; A61L 31/10; A61L 27/36; A61L 27/362; A61L 27/3679; A61L 27/3691; A61L 27/56; A61L 2430/02; A61L 2430/40; A61L 27/24; A61L 27/3604; A61L 27/38; A61L 2430/10; A61L 27/3683; A61L 27/3695; A61L 27/3834; A61L 2300/414; A61L 2400/06; A61L 31/005; A61L 31/128; A61L 31/129; A61L 31/145; A61L 31/146; A61L 2300/426; A61L 2300/606; A61L 2300/64; A61L 2400/18; A61L 2420/02; A61L 2430/20; A61L 27/025; A61L 27/06; A61L 27/10; A61L 27/12; A61L 27/225; A61L 27/227; A61L 27/34; A61L 27/3625; A61L 27/507; C08L 23/12; C08L 27/18; C08L 67/02; A61F 2002/30062; A61F 2002/30069; A61F 2002/30113; A61F 2002/30125; A61F 2002/30574; A61F 2002/30576; A61F 2002/30581; A61F 2002/30588; A61F 2002/30754; A61F 2002/30766; A61F 2002/3092; A61F 2210/0004; A61F 2230/0006; A61F 2230/0008; A61F 2/30756; A61F 2/30942; A61F 2/3099; A61F 2/2415; A61F 2002/075; A61F 2230/005; A61F 2230/0054; A61F 2230/0067; A61F 2/0063; A61F 2/0077; A61F 2/06; A61F 2/07; A61F 2/89; A61F 2/91; A61K 35/36; A61K 38/00;
(Continued)

(56) References Cited

U.S. PATENT DOCUMENTS 3,155,095 A  11/1964 Brown
4,294,241 A  10/1981 Miyata
(Continued)

FOREIGN PATENT DOCUMENTS

CN  103705542 A  4/2014
CN  104837494 A  8/2015
(Continued)

OTHER PUBLICATIONS

Badylak, "Xenogeneic extracellular matrix as a scaffold for tissue reconstruction", Transplant Immunology, 2004, pp. 367-377, vol. 12.

(Continued)

*Primary Examiner* — Michelle F. Paguio Frising
(74) *Attorney, Agent, or Firm* — The Webb Law Firm

(57) ABSTRACT

Provided are methods for preparing sterilized, gelled, solubilized extracellular matrix (ECM) compositions useful as cell growth substrates. Also provided are compositions prepared according to the methods as well as uses for the compositions. In one embodiment a device, such as a prosthesis, is provided which comprises an inorganic matrix into which the gelled, solubilized ECM is dispersed to facilitate in-growth of cells into the ECM and thus adaptation and/or attachment of the device to a patient.

18 Claims, 17 Drawing Sheets

Related U.S. Application Data

(60) Provisional application No. 61/968,716, filed on Mar. 21, 2014.

(51) Int. Cl.
*A61L 27/38* (2006.01)
*A61L 27/50* (2006.01)
*A61L 27/54* (2006.01)

(52) U.S. Cl.
CPC .............. *A61L 27/38* (2013.01); *A61L 27/50* (2013.01); *A61L 27/54* (2013.01); *A61L 2430/02* (2013.01)

(58) Field of Classification Search
CPC ........ A61K 35/12; A61K 35/28; A61K 35/38; A61K 35/22; A61K 35/583; A61K 35/60; A61K 35/616; A61K 35/618; A61K 35/62; A61K 35/63; A61K 35/64; A61K 35/646; A61K 38/1825; A61P 1/00; A61P 35/00; A61P 1/04; A61P 43/00; A61P 9/10; C07K 14/78; C07K 14/745; C07K 14/75; C12N 2533/90; C12N 5/0068; C12N 2509/00; C12P 21/00; Y10S 623/915; Y10S 623/916; Y10S 623/918; A61B 17/3205
See application file for complete search history.

(56) References Cited

U.S. PATENT DOCUMENTS

| | | |
|---|---|---|
| 4,563,350 A | 1/1986 | Nathan et al. |
| 4,582,640 A | 4/1986 | Smestad et al. |
| 4,902,508 A | 2/1990 | Badylak et al. |
| 4,956,178 A | 9/1990 | Badylak et al. |
| 4,970,298 A | 11/1990 | Silver et al. |
| 4,978,668 A | 12/1990 | Babbs et al. |
| 5,007,927 A | 4/1991 | Badylak et al. |
| 5,171,262 A | 12/1992 | MacGregor |
| 5,258,042 A | 11/1993 | Mehta |
| 5,275,826 A | 1/1994 | Badylak et al. |
| 5,281,422 A | 1/1994 | Badylak et al. |
| 5,352,463 A | 10/1994 | Badylak et al. |
| 5,354,274 A | 10/1994 | Demeter et al. |
| 5,372,821 A | 12/1994 | Badylak et al. |
| 5,393,936 A | 2/1995 | Tyhy et al. |
| 5,417,536 A | 5/1995 | Cech |
| 5,445,833 A | 8/1995 | Badylak et al. |
| 5,516,533 A | 5/1996 | Badylak et al. |
| 5,554,389 A | 9/1996 | Badylak et al. |
| 5,573,784 A | 11/1996 | Badylak et al. |
| 5,578,798 A | 11/1996 | Nuyts |
| 5,641,518 A | 6/1997 | Badylak et al. |
| 5,645,860 A | 7/1997 | Knapp, Jr. et al. |
| 5,658,594 A | 8/1997 | Al-Hassan |
| 5,665,391 A | 9/1997 | Lea |
| 5,695,998 A | 12/1997 | Badylak et al. |
| 5,700,486 A | 12/1997 | Canal et al. |
| 5,711,969 A | 1/1998 | Patel et al. |
| 5,730,757 A | 3/1998 | Benetti et al. |
| 5,741,701 A | 4/1998 | Swiderek et al. |
| 5,753,267 A | 5/1998 | Badylak et al. |
| 5,755,791 A | 5/1998 | Whitson et al. |
| 5,762,966 A | 6/1998 | Knapp, Jr. et al. |
| 5,771,969 A | 6/1998 | Garay |
| 5,800,537 A | 9/1998 | Bell |
| 5,817,662 A | 10/1998 | Klein et al. |
| 5,866,414 A | 2/1999 | Badylak et al. |
| 5,885,619 A | 3/1999 | Patel et al. |
| 5,913,876 A | 6/1999 | Taylor et al. |
| 5,925,054 A | 7/1999 | Taylor et al. |
| 5,955,110 A | 9/1999 | Patel et al. |
| 5,968,096 A | 10/1999 | Whitson et al. |
| 5,997,575 A | 12/1999 | Whitson et al. |
| 6,001,111 A | 12/1999 | Sepetka et al. |
| 6,087,157 A | 7/2000 | Badylak et al. |
| 6,096,347 A | 8/2000 | Geddes et al. |
| 6,099,567 A | 8/2000 | Badylak et al. |
| 6,126,686 A | 10/2000 | Badylak et al. |
| 6,171,610 B1 | 1/2001 | Vacanti et al. |
| 6,187,039 B1 | 2/2001 | Hiles et al. |
| 6,214,022 B1 | 4/2001 | Taylor et al. |
| 6,241,774 B1 | 6/2001 | Shimizu |
| 6,241,981 B1 | 6/2001 | Cobb et al. |
| 6,264,992 B1 | 7/2001 | Voytik-Harbin et al. |
| 6,291,240 B1 | 9/2001 | Mansbridge et al. |
| 6,308,104 B1 | 10/2001 | Taylor et al. |
| 6,331,319 B1 | 12/2001 | Badylak et al. |
| 6,375,989 B1 | 4/2002 | Badylak et al. |
| 6,379,710 B1 | 4/2002 | Badylak |
| 6,381,499 B1 | 4/2002 | Taylor et al. |
| 6,444,229 B2 | 9/2002 | Voytik-Harbin et al. |
| 6,448,076 B2 | 9/2002 | Dennis et al. |
| 6,475,232 B1 | 11/2002 | Babbs et al. |
| 6,485,723 B1 | 11/2002 | Badylak et al. |
| 6,551,618 B2 | 4/2003 | Baird et al. |
| 6,554,857 B1 | 4/2003 | Zilla et al. |
| 6,576,265 B1 | 6/2003 | Spievack |
| 6,579,538 B1 | 6/2003 | Spievack |
| 6,602,189 B1 | 8/2003 | Bennetti et al. |
| 6,653,291 B1 | 11/2003 | Badylak et al. |
| 6,696,270 B2 | 2/2004 | Badylak et al. |
| 6,783,776 B2 | 8/2004 | Spievack |
| 6,793,939 B2 | 9/2004 | Badylak |
| 6,849,273 B2 | 2/2005 | Spievack |
| 6,852,339 B2 | 2/2005 | Spievack |
| 6,861,074 B2 | 3/2005 | Spievack |
| 6,884,619 B2 | 4/2005 | Hockfield et al. |
| 6,887,495 B2 | 5/2005 | Spievack |
| 6,890,562 B2 | 5/2005 | Spievack |
| 6,890,563 B2 | 5/2005 | Spievack |
| 6,890,564 B2 | 5/2005 | Spievack |
| 6,893,666 B2 | 5/2005 | Spievack |
| 6,918,396 B1 | 7/2005 | Badylak et al. |
| 6,926,662 B1 | 8/2005 | Aboul-Hosn et al. |
| 6,962,814 B2 | 11/2005 | Mitchell et al. |
| 7,175,841 B2 | 2/2007 | Badylak et al. |
| 7,217,294 B2 | 5/2007 | Kusanagi et al. |
| 7,235,295 B2 | 6/2007 | Laurencin et al. |
| 7,326,571 B2 | 2/2008 | Freyman |
| 7,402,319 B2 | 7/2008 | Schmidt et al. |
| 7,482,025 B2 | 1/2009 | Badylak |
| 7,771,717 B2 | 8/2010 | Badylak et al. |
| 7,776,596 B2 | 8/2010 | Badylak |
| 7,780,725 B2 | 8/2010 | Haug et al. |
| 7,780,950 B2 | 8/2010 | Hazen |
| 7,785,246 B2 | 8/2010 | Aboul-Hosn et al. |
| 7,790,141 B2 | 9/2010 | Pathak et al. |
| 7,795,022 B2 | 9/2010 | Badylak |
| 7,795,218 B2 | 9/2010 | McKerracher et al. |
| 7,795,221 B2 | 9/2010 | Sharma et al. |
| 7,795,242 B2 | 9/2010 | Van Rhijn et al. |
| 7,799,070 B2 | 9/2010 | Bates et al. |
| 7,803,178 B2 | 9/2010 | Whirley et al. |
| 7,803,374 B2 | 9/2010 | Lanza et al. |
| 7,806,857 B2 | 10/2010 | Khosravi et al. |
| 7,811,622 B2 | 10/2010 | Bates et al. |
| 7,815,661 B2 | 10/2010 | Mirizzi et al. |
| 7,815,686 B2 | 10/2010 | Badylak |
| 7,815,946 B1 | 10/2010 | Murthy et al. |
| 7,816,369 B2 | 10/2010 | Guicherit et al. |
| 7,818,084 B2 | 10/2010 | Boyden et al. |
| 7,820,193 B2 | 10/2010 | Hunter et al. |
| 7,820,634 B2 | 10/2010 | Badylak et al. |
| 7,824,698 B2 | 11/2010 | Potts et al. |
| 7,828,840 B2 | 11/2010 | Biggs et al. |
| 7,833,148 B2 | 11/2010 | Noishiki |
| 7,833,978 B2 | 11/2010 | Chaikof et al. |
| 7,837,669 B2 | 11/2010 | Dann et al. |
| 7,837,726 B2 | 11/2010 | Von Oepen et al. |
| 7,840,263 B2 | 11/2010 | Girouard et al. |
| 7,846,138 B2 | 12/2010 | Dann et al. |
| 7,846,202 B2 | 12/2010 | Bates et al. |

(56) References Cited

U.S. PATENT DOCUMENTS

| | | |
|---|---|---|
| 7,850,645 B2 | 12/2010 | Atanasoska et al. |
| 7,850,676 B2 | 12/2010 | Wood, Jr. |
| 7,850,729 B2 | 12/2010 | Melvin |
| 7,851,189 B2 | 12/2010 | Freyman et al. |
| 7,854,743 B2 | 12/2010 | Palasis et al. |
| 7,854,759 B2 | 12/2010 | Shirley |
| 7,854,944 B2 | 12/2010 | Mandrusov et al. |
| 7,858,296 B2 | 12/2010 | Sowemimo-Coker et al. |
| 7,862,605 B2 | 1/2011 | Ragheb et al. |
| 7,867,169 B2 | 1/2011 | Webler et al. |
| 7,867,217 B2 | 1/2011 | Wood, Jr. |
| 7,867,275 B2 | 1/2011 | Bates et al. |
| 7,871,402 B2 | 1/2011 | Wood, Jr. |
| 7,872,068 B2 | 1/2011 | Khosravi et al. |
| 7,875,017 B2 | 1/2011 | Sabbah |
| 7,875,272 B2 | 1/2011 | Messina et al. |
| 7,875,273 B2 | 1/2011 | Messina et al. |
| 7,877,142 B2 | 1/2011 | Moaddeb et al. |
| 7,878,978 B2 | 2/2011 | Conrad et al. |
| 7,879,023 B2 | 2/2011 | Wood, Jr. |
| 7,879,062 B2 | 2/2011 | Galdonik et al. |
| 7,879,067 B2 | 2/2011 | Galdonik et al. |
| 7,879,576 B2 | 2/2011 | Fenical et al. |
| 7,892,214 B2 | 2/2011 | Kagan et al. |
| 7,892,246 B2 | 2/2011 | Akin et al. |
| 7,919,112 B2 | 4/2011 | Pathak et al. |
| 7,919,121 B2 | 4/2011 | Badylak et al. |
| 8,003,131 B2 | 8/2011 | Badylak |
| 8,021,692 B2 | 9/2011 | Hiles et al. |
| 8,029,774 B2 | 10/2011 | Beckman et al. |
| 8,084,048 B2 | 12/2011 | Badylak |
| 8,192,763 B2 | 6/2012 | Johnson |
| 8,241,908 B2 | 8/2012 | Qian et al. |
| 8,257,434 B2 | 9/2012 | Matheny |
| 8,298,586 B2 | 10/2012 | Bosley, Jr. et al. |
| 8,361,503 B2 | 1/2013 | Badylak et al. |
| 8,409,275 B2 | 4/2013 | Matheny |
| 8,409,625 B2 | 4/2013 | Badylak |
| 8,449,607 B2 | 5/2013 | Matheny |
| 8,465,771 B2 | 6/2013 | Wan et al. |
| 8,535,719 B2 | 9/2013 | Badylak et al. |
| 8,540,615 B2 | 9/2013 | Aboul-Hosn et al. |
| 8,597,674 B2 | 12/2013 | Chu et al. |
| 8,608,796 B2 | 12/2013 | Matheny |
| 8,637,067 B1 | 1/2014 | Sun et al. |
| 8,647,677 B2 | 2/2014 | Badylak et al. |
| 8,673,295 B2 | 3/2014 | Fuijimoto et al. |
| 8,679,176 B2 | 3/2014 | Matheny |
| 8,691,276 B2 | 4/2014 | Badylak et al. |
| 8,696,744 B2 | 4/2014 | Matheny et al. |
| 8,709,076 B1 | 4/2014 | Matheny et al. |
| 8,716,438 B2 | 5/2014 | Agrawal et al. |
| 8,741,352 B2 | 6/2014 | Hodde et al. |
| 8,771,294 B2 | 7/2014 | Sepetka et al. |
| 8,802,436 B1 | 8/2014 | Kentner et al. |
| 8,834,344 B2 | 9/2014 | Aboul-Hosn et al. |
| 8,852,637 B2 | 10/2014 | Naughton et al. |
| 8,871,511 B1 | 10/2014 | Matheny et al. |
| 8,877,224 B2 | 11/2014 | Matheny et al. |
| 8,889,791 B2 | 11/2014 | Guan et al. |
| 8,895,304 B2 | 11/2014 | Fette et al. |
| 8,906,631 B2 | 12/2014 | Clevers et al. |
| 8,927,003 B2 | 1/2015 | Badylak et al. |
| 8,940,292 B2 | 1/2015 | Atala et al. |
| 8,974,542 B2 | 3/2015 | Fujimoto et al. |
| 8,975,075 B2 | 3/2015 | Fette et al. |
| 8,980,296 B2 | 3/2015 | Matheny et al. |
| 9,011,526 B2 | 4/2015 | Matheny |
| 9,023,972 B2 | 5/2015 | Chu et al. |
| 9,034,386 B2 | 5/2015 | Flynn |
| 9,044,319 B2 | 6/2015 | Matheny |
| 9,060,969 B2 | 6/2015 | Matheny |
| 9,078,873 B2 | 7/2015 | Matheny |
| 9,078,882 B2 | 7/2015 | Matheny |
| 9,079,965 B2 | 7/2015 | Zhou et al. |
| 9,084,841 B2 | 7/2015 | Matheny |
| 9,089,549 B2 | 7/2015 | Matheny |
| 9,119,831 B2 | 9/2015 | Kentner et al. |
| 9,119,841 B2 | 9/2015 | Matheny |
| 9,119,899 B2 | 9/2015 | Matheny |
| 9,161,952 B2 | 10/2015 | Matheny et al. |
| 9,186,435 B2 | 11/2015 | Hiles |
| 9,216,236 B2 | 12/2015 | Machluf et al. |
| 9,226,996 B2 | 1/2016 | Moro et al. |
| 9,238,091 B2 | 1/2016 | Kentner et al. |
| 9,277,999 B2 | 3/2016 | Badylak et al. |
| 9,314,340 B2 | 4/2016 | Badylak et al. |
| 9,340,602 B2 | 5/2016 | Agrawal et al. |
| 9,364,580 B2 | 6/2016 | Moro et al. |
| 9,421,307 B2 | 8/2016 | Amoroso et al. |
| 9,433,701 B2 | 9/2016 | Spievack |
| 9,474,829 B2 | 10/2016 | Kentner et al. |
| 9,480,776 B2 | 11/2016 | Badylak et al. |
| 9,510,933 B2 | 12/2016 | Ingham et al. |
| 9,522,216 B2 | 12/2016 | Moro et al. |
| 9,538,996 B2 | 1/2017 | Patel et al. |
| 9,597,358 B2 | 3/2017 | Du et al. |
| 9,795,713 B2 | 10/2017 | Kentner et al. |
| 9,814,744 B2 | 11/2017 | Badylak et al. |
| 9,848,987 B2 | 12/2017 | Badylak et al. |
| 9,861,662 B2 | 1/2018 | Badylak et al. |
| 9,938,502 B2 | 4/2018 | Zhang et al. |
| 10,004,827 B2 | 6/2018 | Badylak et al. |
| 10,005,827 B2 | 6/2018 | Spetzler et al. |
| 10,092,676 B2 | 10/2018 | Amoroso et al. |
| 10,213,526 B2 * | 2/2019 | Badylak ................ A61L 27/50 |
| 10,286,119 B2 * | 5/2019 | Badylak ................ A61L 31/048 |
| 10,729,813 B2 | 8/2020 | Badylak et al. |
| 10,736,991 B2 | 8/2020 | Badylak et al. |
| 2001/0014475 A1 | 8/2001 | Frondoza et al. |
| 2002/0085994 A1 | 7/2002 | Ceres et al. |
| 2002/0090725 A1 | 7/2002 | Simpson et al. |
| 2002/0115208 A1 | 8/2002 | Mitchell et al. |
| 2003/0012822 A1 | 1/2003 | Voytik-Harbin et al. |
| 2003/0036797 A1 | 2/2003 | Malaviya et al. |
| 2003/0036801 A1 | 2/2003 | Schwartz et al. |
| 2003/0100944 A1 | 5/2003 | Laksin et al. |
| 2004/0009600 A1 | 1/2004 | Bowlin et al. |
| 2004/0076657 A1 | 4/2004 | Wolfinbarger, Jr. et al. |
| 2004/0078076 A1 | 4/2004 | Badylak et al. |
| 2004/0175366 A1 | 9/2004 | Badylak |
| 2004/0176855 A1 | 9/2004 | Badylak |
| 2004/0187877 A1 | 9/2004 | Badylak et al. |
| 2004/0191226 A1 | 9/2004 | Badylak |
| 2005/0013870 A1 | 1/2005 | Freyman et al. |
| 2005/0013872 A1 | 1/2005 | Freyman |
| 2005/0181016 A1 | 8/2005 | Freyman et al. |
| 2006/0134079 A1 | 6/2006 | Sih et al. |
| 2006/0136028 A1 | 6/2006 | Ross et al. |
| 2006/0147433 A1 | 7/2006 | Hiles |
| 2006/0149309 A1 | 7/2006 | Paul et al. |
| 2006/0153815 A1 | 7/2006 | Seyda et al. |
| 2006/0201996 A1 | 9/2006 | Hodde |
| 2007/0014755 A1 | 1/2007 | Beckman et al. |
| 2007/0014773 A1 | 1/2007 | Matheny et al. |
| 2007/0014860 A1 | 1/2007 | Rosenthal et al. |
| 2007/0014870 A1 | 1/2007 | Matheny |
| 2007/0014871 A1 | 1/2007 | Matheny |
| 2007/0014872 A1 | 1/2007 | Matheny et al. |
| 2007/0014873 A1 | 1/2007 | Matheny |
| 2007/0014874 A1 | 1/2007 | Matheny |
| 2007/0135906 A1 | 6/2007 | Badylak et al. |
| 2007/0082060 A1 | 8/2007 | Hiles et al. |
| 2007/0196380 A1 | 8/2007 | Firestone |
| 2008/0069852 A1 | 3/2008 | Shimp et al. |
| 2008/0107750 A1 | 5/2008 | Hodde et al. |
| 2008/0260831 A1 | 10/2008 | Badylak et al. |
| 2008/0268019 A1 | 10/2008 | Badylak et al. |
| 2008/0312340 A1 | 12/2008 | Hobson et al. |
| 2009/0035855 A1 | 2/2009 | Ying et al. |
| 2009/0053279 A1 | 2/2009 | Badylak et al. |
| 2009/0138074 A1 | 5/2009 | Freyman et al. |
| 2009/0204228 A1 | 8/2009 | Hiles |
| 2009/0240337 A1 | 9/2009 | Myung et al. |

(56) References Cited

U.S. PATENT DOCUMENTS

| | | |
|---|---|---|
| 2010/0047305 A1 | 2/2010 | Naughton et al. |
| 2010/0119577 A1 | 5/2010 | Min et al. |
| 2010/0196480 A1 | 8/2010 | Hiles et al. |
| 2010/0222882 A1* | 9/2010 | Badylak .............. A61F 2/30756 623/14.12 |
| 2010/0226895 A1 | 9/2010 | Boruch |
| 2010/0266654 A1 | 10/2010 | Hodde et al. |
| 2011/0097403 A1 | 4/2011 | Naughton et al. |
| 2011/0151011 A1 | 6/2011 | Flynn |
| 2011/0165676 A1 | 7/2011 | Hopkins |
| 2011/0184439 A1 | 7/2011 | Anderson |
| 2011/0195052 A1 | 8/2011 | Behnam et al. |
| 2011/0224484 A1 | 9/2011 | Case et al. |
| 2012/0114755 A1 | 5/2012 | Amadio et al. |
| 2012/0165264 A1 | 6/2012 | Malessa et al. |
| 2012/0165957 A1 | 6/2012 | Everland et al. |
| 2012/0230966 A1 | 9/2012 | Crawford et al. |
| 2012/0264190 A1 | 10/2012 | Christman et al. |
| 2013/0028984 A1 | 1/2013 | Xu et al. |
| 2013/0062127 A1 | 3/2013 | Pangrazio et al. |
| 2013/0202563 A1 | 8/2013 | Badylak et al. |
| 2014/0271491 A1 | 9/2014 | Gittard et al. |
| 2014/0309739 A1 | 10/2014 | Badylak et al. |
| 2014/0356331 A1 | 12/2014 | Badylak et al. |
| 2015/0037436 A1 | 2/2015 | Huang et al. |
| 2016/0045552 A1 | 2/2016 | Ramer et al. |
| 2017/0049932 A1 | 2/2017 | Badylak et al. |
| 2018/0043057 A1 | 2/2018 | Kentner et al. |
| 2018/0200405 A1 | 7/2018 | Badylak et al. |
| 2018/0243473 A1 | 8/2018 | Badylak et al. |
| 2019/0015552 A1 | 1/2019 | Badylak et al. |
| 2019/0076574 A1 | 3/2019 | Ramer et al. |
| 2019/0117837 A1 | 4/2019 | Badylak et al. |
| 2020/0009187 A1 | 1/2020 | Badylak et al. |
| 2020/0030495 A1 | 1/2020 | Badylak et al. |
| 2020/0069738 A1 | 3/2020 | Badylak et al. |
| 2020/0261624 A1 | 8/2020 | Crapo et al. |
| 2021/0106526 A1 | 4/2021 | Badylak et al. |

FOREIGN PATENT DOCUMENTS

| | | |
|---|---|---|
| CN | 104225667 B | 2/2017 |
| CN | 104971380 B | 12/2017 |
| EP | 2873429 B1 | 12/2017 |
| GB | 1602339 A | 11/1981 |
| JP | S545019 A | 1/1979 |
| JP | 6330023 B2 | 6/1988 |
| WO | 1994011008 A1 | 5/1994 |
| WO | 1998001112 A1 | 1/1998 |
| WO | 2000032209 A2 | 6/2000 |
| WO | 2003059284 A2 | 7/2003 |
| WO | 2005020847 A2 | 3/2005 |
| WO | 2006026325 A2 | 3/2006 |
| WO | 2008146956 A1 | 12/2008 |
| WO | 2010056378 A2 | 5/2010 |
| WO | 2011003422 A1 | 1/2011 |
| WO | 2011011482 A2 | 1/2011 |
| WO | 2011041240 A1 | 4/2011 |
| WO | 2011072393 A1 | 6/2011 |
| WO | 2011087743 A2 | 7/2011 |
| WO | 2011109712 A2 | 9/2011 |
| WO | 2012064606 A2 | 5/2012 |
| WO | 2013009595 A2 | 1/2013 |

OTHER PUBLICATIONS

Chan et al., "Viscosities of Injectable Biomaterials in Vocal Augmentation Surgery", NCVS Status and Progress Report, May 1997, pp. 119-126, vol. 11.

Dejardin et al., "Tissue-Engineered Rotator Cuff Tendon Using Porcine Small Intestine Submucosa Histologic and Mechanical Evaluation in Dogs", The American Journal of Sports Medicine, 2001, pp. 175-184, vol. 29:2.

Freytes et al., "Biaxial strength of multilaminated extracellular matrix scaffolds", Biomaterials, 2004, pp. 2353-2361, vol. 25.

Gelman et al., "Collagen Fibril Formation Evidence for a Multistep Process", The Journal of Biological Chemistry, Jan. 10, 1979, pp. 180-186, vol. 254:1.

Hacking et al., "Fibrous tissue ingrowth and attatchment to porous tantalum", 2000, John Wiley & Sons, Inc., pp. 631-638.

Higuera et al., "Tendon reattachment to a metallic implant using an allogenic bone plate augmented with rhOP-1 vs. autogenous cancellous bone and marrow in a canine model", Journal of Orthopaedic Research, 2005, pp. 1091-1099, vol. 23.

Hodde et al., "Effects of terilization on an extracellular matrix scaffold: Part I. Composition and matrix architecture", J Mater Sci: Mater Med, 2007, pp. 537-543, vol. 18.

Klemuk et al., "Viscoelastic Properties of Three Vocal-Fold Injectable Biomaterials at Low Audio Frequencies", The Laryngoscope, Sep. 2004, pp. 1597-1603, vol. 114.

Marieb, Human Anatomy and Physiology, Second Edition, The Benjamin Cummings, Publishing Company, Inc., Redwood City, California, 1992, pp. 792-793, 802-803.

Reddy et al., "A Simplified Method for the Analysis of Hydroproline in Biological Tissues", Clinical Biochemistry, 1996, pp. 225-229, vol. 29:3.

Ringel et al., "The Application of Tissue Engineering Procedures to Repair the Larynx", Journal of Speech, Language, and Hearing Research, Feb. 2006, pp. 194-208, vol. 49.

Sarikaya et al., "Antimicrobial Activity Associated with Extracellular Matrices", Tissue Engineering, 2002, pp. 63-71, vol. 8:1.

White et al., "Effective terminal sterilization using supercritical carbon dioxide", Journal of Biotechnology, 2006, pp. 504-515, vol. 123.

Badylak, "The extracellular matrix as a scaffold for tissue reconstruction," 2002, Seminars in Cell & Developmental Biology, vol. 13, pp. 377-383.

Badylak, "Xenogenic extracellular matrix as a scaffold for tissue reconstruction," 2004, Transpl Immunol., vol. 12, pp. 367-377.

Badylak et al., "Regenerative medicine and developmental biology: the role of the extracellular matrix," 2005, Anat Rec B New Anat., vol. 287, No. 1, pp. 36-41.

Badylak, "The extracellular matrix as a biologic scaffold material," 2007, Biomaterials, vol. 28, pp. 3587-3593.

Badylak et al., "Extracellular matrix as a biological scaffold material: Structure and function", 2009, Acta Biomaterialia, vol. 5, pp. 1-13.

Badylak et al., "Biologic scaffolds for constructive tissue remodeling," 2011, Biomaterials, vol. 32, No. 1, pp. 316-319.

Choi et al., "Human extracellular matrix (ECM) powders for injectable cell delivery and adipose tissue engineering," 2009, J. Controlled Release, vol. 139, pp. 2-7.

Crapo et al., "Small Intestinal Submucosa Gel as a Potential Scaffolding Material for Cardiac Tissue Engineering," 2010, Acta Biomater., vol. 6, No. 6, pp. 2091-2096.

Crapo et al., "An Overview of Tissue and Whole Organ Decellularization Processes," 2011, Biomaterials, vol. 32, No. 12, pp. 3233-3243.

DeQuach et al., "Injectable skeletal muscle matrix hydrogel promotes neovascularization and muscle cell infiltration n a hindlimb ischemia model," 2012, Eur Cell Mater., vol. 23, pp. 400-412.

Faulk et al., "ECM hydrogel coating mitigates the chronic inflammatory response to polypropylene mesh," 2014, Biomaterials, vol. 35, pp. 8585-8595.

Freytes et al., "Porcine Urinary Bladder Matrix Derived Gel for Tissue Engineering Applications," 2006, Regenerate World Congress and Society for Biomaterials: 2006, Poster and Abstract.

Freytes et al., "Hydrated versus lyophilized forms of porcine extracellular matrix derived from urinary bladder," 2008, J Biomed Mater Res. A, vol. 87, No. 4, pp. 862-872.

Freytes et al., "Preparation and rheological characterization of a gel form of the porcine urinary bladder matrix," 2008, Biomaterials, vol. 29, pp. 1630-1637.

Gilbert et al., "Production and characterization of ECM powder: Implications for tissue engineering applications," 2005, Biomaterials, vol. 26, pp. 1431-1435.

(56) References Cited

OTHER PUBLICATIONS

Gilbert et al., "Decellularization of tissues and organs," 2006, Biomaterials, vol. 27, pp. 3675-3683.
Gilbert et al., "Development of a Hybrid ECM/Porous Metal Scaffold for Connective Tissue Ingrowth," 2006, Regenerate World Congress Meeting: Apr. 2006, Poster and Abstract.
Hong et al., "Mechanical properties and in vivo behavior of a biodegradable synthetic polymer microfiber-extracellular matrix hydrogel biohybrid scaffold," 2011, Biomaterials, vol. 32, pp. 3387-3394.
Keane et al., "Preparation and Characterization of a Biologic Scaffold from Esophageal Mucosa," 2013, Biomaterials, vol. 34, No. 28, pp. 6729-6737.
Keane et al., "Methods of tissue decellularization used for preparation of biologic scaffolds and in vivo relevance," 2015, Methods, vol. 84, pp. 25-34.
Keane et al.," I issue-specific effects of esophageal extracellular matrix," 2015, Tissue Eng. Part A, vol. 21, Nos. 17-18, pp. 2293-2300.
Medberry et al., "Hydrogels Derived from Central Nervous System Extracellular Matrix," 2013, Biomaterials, vol. 34, No. 4, pp. 1033-1040.
Sawkins et al., "Hydrogels derived from demineralized and decellularized bone extracellular matrix," 2013, Acta Biomateriala, vol. 9, pp. 7865-7873.
Seif-Naraghi et al., "Design and Characterization of an Injectable Pericardial Matrix Gel: A Potentially Autologous Scaffold for Cardiac Tissue Engineering," 2010, Tissue Eng Part A, vol. 16, No. 6, pp. 2017-2027.
Sicari et al., "The promotion of a constructive macrophage phenotype by solubilized extracellular matrix," 2014, Biomaterials, vol. 35, pp. 8605-8612.
Singelyn et al., "Naturally derived myocardial matrix as an injectable scaffold for cardiac tissue engineering," 2009, Biomaterials, vol. 30, pp. 5409-5416.
Slivka et al., "Fractionation of an ECM hydrogel into structural and soluble components reveals distinctive roles in egulating macrophage behavior," 2014, Biomaterials Science, vol. 2, pp. 1521-1534.
Stuart et al., "Characterization of Gels Composed of Blends of Collagen I, Collagen III, and Chondroitin Sulfate," 2009, Biomacromolecules, vol. 10, No. 1, pp. 25-31.
Wolf et al., "A hydrogel derived from decellularized dermal extracellular matrix," 2012, Biomaterials, vol. 33, pp. 7028-7038.
Wood et al., "Use of a particulate extracellular matrix bioscaffold for treatment of acquired urinary incontinence in dogs," 2015, J Am Vet Med Assoc., vol. 226, No. 7, pp. 1095-1097.

\* cited by examiner

Col I 4 mg/ml    UBM 4 mg/ml    UBM 8 mg/ml

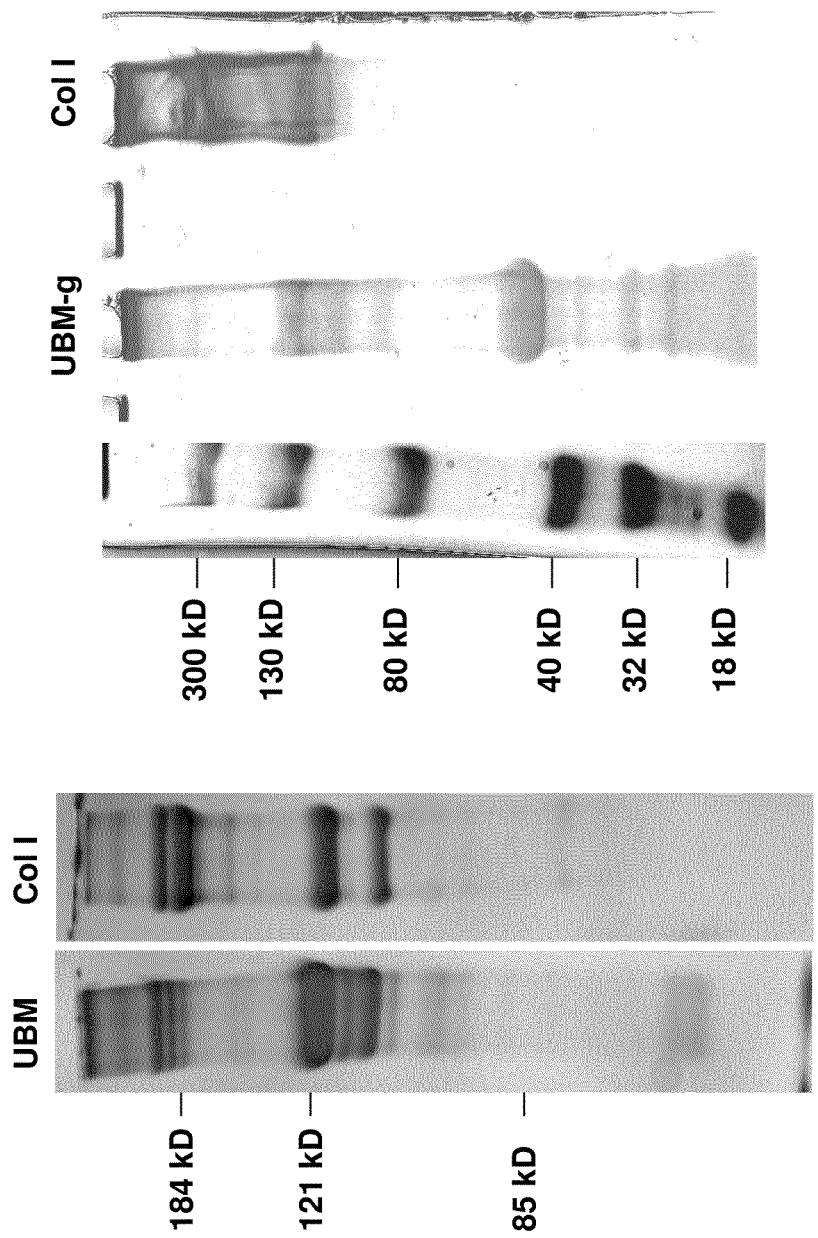

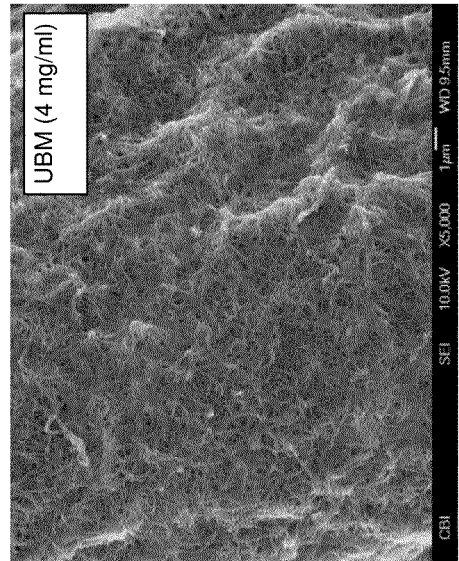
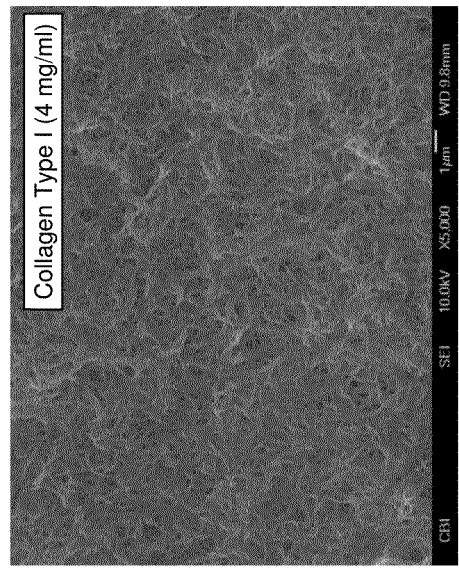
Fig. 7A
Fig 7B

| lyophilized | 0.01N HCl reconstituted | ddH$_2$O reconstituted | EtO sterilized: reconstituted in water | ddH₂O reconstituted
SIS-ECM pre-gel ddH₂O reconstituted
UBM pre-gel

METHODS FOR PREPARATION OF A TERMINALLY STERILIZED HYDROGEL DERIVED FROM EXTRACELLULAR MATRIX

CROSS-REFERENCE TO RELATED APPLICATIONS

This application is Continuation of U.S. patent application Ser. No. 15/127,707 filed Sep. 20, 2016, which is a national stage of International Patent Application No. PCT/US2015/021732, filed Mar. 20, 2015, which claims the benefit of U.S. Provisional Patent Application No. 61/968,716, filed Mar. 21, 2014, each of which is incorporated herein by reference in its entirety.

BACKGROUND

Methods of sterilization of extracellular matrix- (ECM-) derived gels are described herein.

Terminal sterilization of extracellular matrix (ECM) scaffolds (e.g. by exposure to ethylene oxide (EtO) gas, gamma irradiation, or electron beam radiation) inhibits the formation of an ECM derived hydrogel. Results of preclinical studies have shown and continue to display marked benefits of ECM degradation products, which are concentrated in ECM hydrogels. A method of sterilization of ECM hydrogels must be identified prior to clinical translation and widespread commercialization of hydrogel products.

SUMMARY

Described herein are methods of making ECM gels and related compositions. ECM gels do not typically produce gels after digestion of terminally sterilized ECM material with an acid protease to produce a digest solution, followed by neutralization and raising the temperature of the solution to 37° C. Described herein is a solution to this problem, which permits terminal sterilization, yet also results in reproducible gelation. ECM scaffolds terminally sterilized via EtO, electron beam, and gamma radiation at multiple doses in a solid sheet form do not support hydrogel formation. However, we show herein that changing the form of material prior to sterilization from sheet to a lyophilized ECM digest is conducive to hydrogel formation. As shown in the Examples below, for example and without limitation, freeze-drying (lyophilizing) an ECM digest, sterilizing the dried digest by exposure to ethylene oxide gas, and reconstituting the dried pre-gel in water, produces a digest that reproducibly gels when neutralized and incubated at 37° C. Based on these results, terminal sterilization of the dried digest by other accepted methodologies (e.g., electron beam radiation, gamma radiation, x-ray, super-critical carbon dioxide) is expected to similarly allow formation of an ECM hydrogel.

Provided are methods for preparing sterilized, gelled, solubilized extracellular matrix (ECM) compositions useful as cell growth scaffolds. The compositions can be molded prior to implantation or administered to a patient in an un-gelled form prior to gelation where the composition gels in situ. Also provided are compositions prepared according to the methods as well as uses for the compositions. In one embodiment, a device, such as a prosthesis, is provided which comprises an inorganic matrix into which the sterilized, gelled, solubilized ECM is dispersed to facilitate in-growth of cells into the ECM and thus adaptation and/or attachment of the device to a patient.

BRIEF DESCRIPTION OF THE DRAWINGS

FIG. 5 shows results from gel-electrophoresis of UBM and Col I gels.

FIG. 7A is an SEM image of a 4 mg/ml Col I gel at a magnification of 5,000×.

FIG. 7B is an SEM image of a 4 mg/ml UBM gel at a magnification of 5,000×.

DETAILED DESCRIPTION

Figure 1:
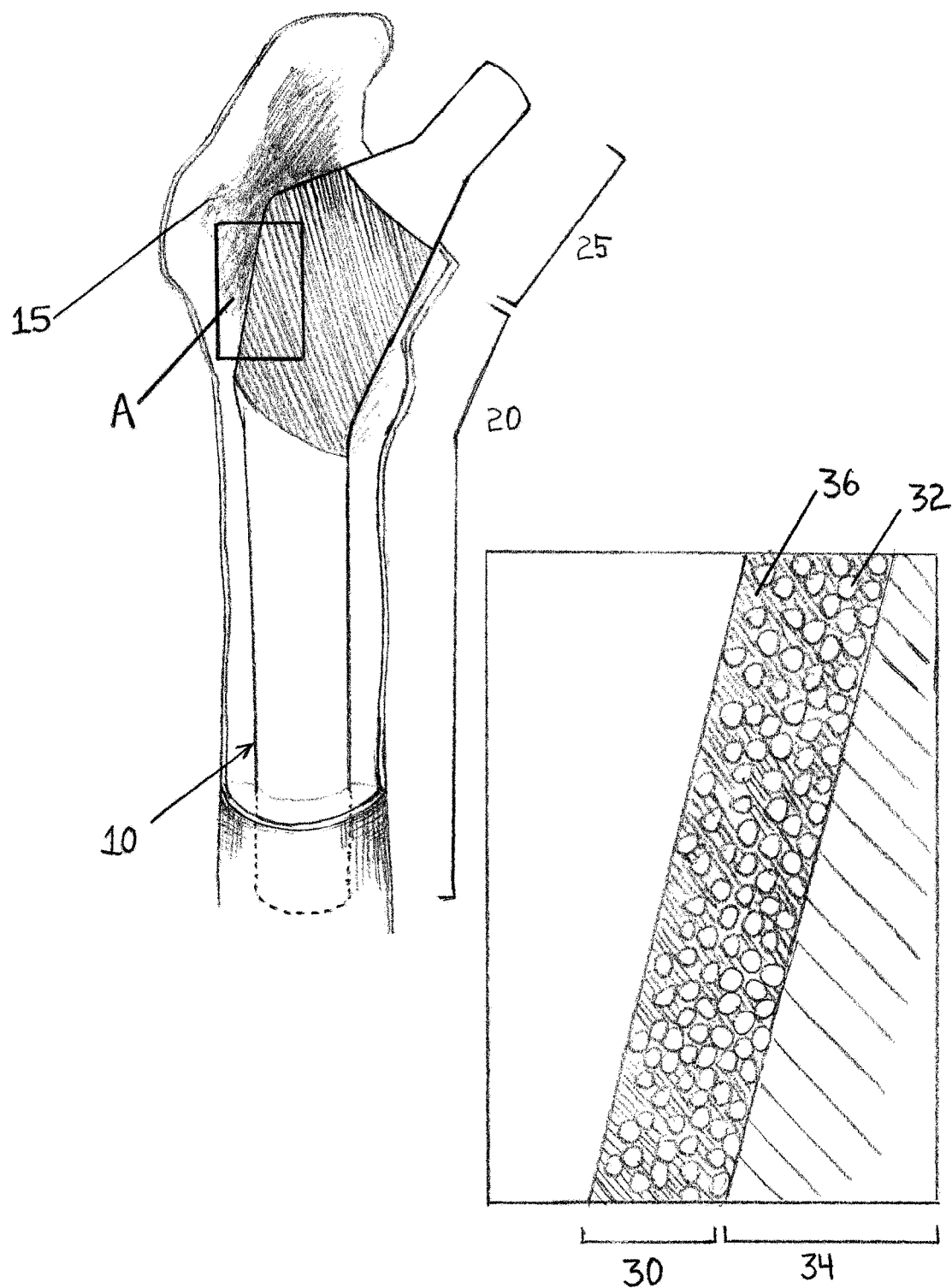
FIG. 1 shows schematically one embodiment of a femoral implant described herein.

The use of numerical values in the various ranges specified in this application, unless expressly indicated otherwise, are stated as approximations as though the minimum and maximum values within the stated ranges are both preceded by the word "about". In this manner, slight variations above and below the stated ranges can be used to achieve substantially the same results as values within the ranges. Also, unless indicated otherwise, the disclosure of ranges is intended as a continuous range including every value between the minimum and maximum values. As used herein "a" and "an" refer to one or more.

As used herein, the term "comprising" is open-ended and may be synonymous with "including", "containing", or "characterized by". The term "consisting essentially of" limits the scope of a claim to the specified materials or steps and those that do not materially affect the basic and novel characteristic(s) of the claimed invention. The term "consisting of" excludes any element, step, or ingredient not specified in the claim. As used herein, embodiments "comprising" one or more stated elements or steps also include, but are not limited to embodiments "consisting essentially of" and "consisting of" these stated elements or steps.

Methods are described herein of preparing extracellular matrix (ECM)-derived compositions comprising solubilized extracellular matrix obtained from any of a variety of tissues. Related compositions, devices and methods of use also are described. The compositions are reverse gelling, meaning that the viscosity of the matrix increases when warmed above the lower critical solution temperature (LCST) of the composition to physiological temperatures approaching about 37° C. According to one non-limiting embodiment, the ECM-derived composition is an injectable solution at temperatures lower than 37° C., but a gel at a physiological temperature of 37° C. According to certain embodiments, the gel is bioactive because the entire, intact ECM is solubilized and is not dialyzed, cross-linked and/or otherwise treated to remove or otherwise inactivate ECM structural or functional components, resulting in a highly bioactive gel scaffold. A general set of principles for preparing an ECM-derived gel is provided along with specific protocols for preparing gels from numerous tissues, including urinary bladder, spleen, liver, heart, pancreas, ovary, small intestine, large intestine, colon, central nervous system (CNS), adipose tissue and bone. Non-limiting examples of reverse-gelling ECM-derived compositions are described in U.S. Pat. No. 8,361,503, and United States Patent Publication Nos. 2010-0226895, and International Patent Publication Nos. WO 2011/087743 and WO 2013/009595.

As used herein, "terminal sterilization" or "terminally sterilized" refers to the essentially or practically complete sterilization of a composition or device. This does not include disinfection, e.g., with peracetic acid during preparation of an ECM product as part of or ancillary to decellularization. For example, an ECM composition can be disinfected by immersion in 0.1% (v/v) peracetic acid (σ), 4% (v/v) ethanol, and 96% (v/v) sterile water for 2 h. The ECM material is then washed twice for 15 min with PBS (pH=7.4) and twice for 15 min with deionized water. Although this is characterized as disinfection, it is typically not acceptable under current regulatory practice as a terminal sterilization method. During terminal sterilization, products are exposed to a validated process that kills living microorganisms. In the context of ECM products, decellularized ECM material can be exposed to terminal sterilization before solubilization, storage and/or commercial distribution. A variety of methods for terminal sterilization are known in the art, including exposure to: ethylene oxide, propylene oxide, gamma radiation, electron beam radiation, gas plasma sterilization, and supercritical carbon dioxide (see, e.g., White, A, et al., "Effective Terminal Sterilization Using Supercritical Carbon Dioxide," (2006) *J. Biotech.* 123(4):504-515).

The composition may also be disinfected by treatment with glutaraldehyde, which causes cross linking of the protein material, but this treatment substantially alters the material such that it is slowly resorbed or not resorbed at all and incites a different type of host remodeling which more closely resembles scar tissue formation or encapsulation rather than constructive remodeling. Cross-linking of the protein material can also be induced with carbodiimide or dehydrothermal or photooxidation methods. Cross-linked ECM material is not considered to be intact ECM for purposes herein.

As indicated in the Examples below, the timing of terminal sterilization substantially affects the ability of a digested, solubilized ECM material to form a hydrogel by reverse gelling. Sterilization is performed on a dry, acid protease-digested ECM composition. By "dry" or "dried" it is meant dried or lyophilized to a point that essentially all water is removed from a composition, recognizing that in practice, one may not literally remove all water molecules from any composition. Thus "dry" or "dried" refers to a water content of, for example and without limitation, less than 5.0, 1.0, 0.5, 0.1, 0.01, 0.001 or 0.0001% by weight of the composition (% wt.). Material can be dried by any process, such as, for example and without limitation, by simple evaporation at any non-damaging temperature, such as at room temperature, or by lyophilization (freeze drying).

According to one embodiment, a method of preparing an extracellular matrix-derived gel is provided. In the method, extracellular matrix (ECM), e.g., intact ECM, is solubilized by digestion with an acid protease such as trypsin or pepsin in an acidic solution to produce a digest solution. The digest solution is dried, for example by air drying or lyophilization. Once the solution is dried, it is terminally sterilized, for example by electron beam or gamma radiation, exposure to ethylene oxide gas or to supercritical carbon dioxide. The composition can be stored, packaged and/or distributed in this dried, e.g., lyophilized, state. The sterilized material is then hydrated, for instance by solubilization in water or in an aqueous solution such as a TRIS buffer or PBS, or a salt solution such as a sodium chloride solution, such as (0.9%) saline to produce a sterilized digest solution. The sterilized digest solution is then brought to a pH between 7.2 and 7.8 to produce a neutralized digest solution, for example, by mixing the solution with an isotonic buffer or a base, such as, without limitation NaOH. The solution gels at a temperature greater than 25° C. The rehydration, neutralization and optionally the gelling step may be combined by rehydrating the dried, sterilized composition in a buffer, such as PBS at pH 7.2-7.8, which will accomplish the rehydration and neutralization step concurrently, and if the rehydration solution is above 25° C., the solution would begin to gel. It may be desirable to maintain the temperature at less than 20-25° C. to control the gelation process, and to more uniformly rehydrate the composition.

The compositions described herein find use as, without limitation, an injectable graft (e.g., xenogeneic, allogeneic or autologous) for tissues, for example, bone or soft tissues, in need of repair or augmentation most typically to correct trauma or disease-induced tissue defects. The compositions also may be used as a filler for implant constructs comprising, for example, a molded construct formed into a desired shape for use in cosmetic or trauma-treating surgical procedures.

The compositions may be implanted into a patient, human or animal, by a number of methods. In one non-limiting embodiment, the compositions are injected as a liquid into a desired site in the patient. As used herein, the term "seed," "seeding," or "seeded" refers to the addition, incorporation, propagation of, or spreading of a defined volume of a cell suspension or a defined cell number into a specific composition. The composition may be pre-seeded with cells, and then preferably injected using a larger-bore, e.g. 16 gauge needle, to prevent shearing of cells. In another non-limiting embodiment, the composition is gelled within a mold, and the gelled, molded product is then implanted into the patient at a desired site. The gelled, molded product may be pre-seeded (laid onto the molded gel or mixed in during gelation) with cells, such as cells of the patient.

As used herein, the terms "extracellular matrix" and "ECM" refer to a natural scaffolding for cell growth that is prepared by decellularization of tissue found in multicellular organisms, such as mammals and humans. ECM can be further processed by, for instance dialysis or cross-linking. ECM is a complex mixture of structural and non-structural biomolecules, including, but not limited to, collagens, elastins, laminins, glycosaminoglycans, proteoglycans, antimicrobials, chemoattractants, cytokines, and/or growth factors. In mammals, ECM often comprises about 90% collagen, in its various forms. The composition and structure of ECMs vary depending on the source of the tissue. For example, small intestine submucosa (SIS), urinary bladder matrix (UBM) and liver stroma ECM each differ in their overall structure and composition due to the unique cellular niche needed for each tissue.

As used herein, the terms "intact extracellular matrix" and "intact ECM" refers to an extracellular matrix that retains activity of its structural and non-structural biomolecules, including, but not limited to, collagens, elastins, laminins, glycosaminoglycans, proteoglycans, antimicrobials, chemoattractants, cytokines, and/or growth factors, such as, without limitation comminuted ECM as described herein. The activity of the biomolecules within the ECM can be removed chemically or mechanically, for example, by cross-linking and/or by dialyzing the ECM. Intact ECM essentially has not been cross-linked and/or dialyzed, meaning that the ECM has not been subjected to a dialysis and/or a cross-linking process, or conditions other than processes that occur naturally during storage and handling of ECM prior to solubilization, as described herein. Thus, ECM that is substantially cross-linked and/or dialyzed (in anything but a trivial manner which does not substantially affect the gelation and functional characteristics of the ECM in its uses described herein) is not considered to be "intact".

By "biocompatible", it is meant that a device, scaffold composition, etc. is essentially, practically (for its intended use) and/or substantially non-toxic, non-injurious or non-inhibiting or non-inhibitory to cells, tissues, organs, and/or organ systems that would come into contact with the device, scaffold, composition, etc.

In general, the method of preparing an ECM-derived gel requires the isolation of ECM from an animal of interest and from a tissue or organ of interest. In certain embodiments, the ECM is isolated from mammalian tissue. As used herein, the term "mammalian tissue" refers to tissue derived from a mammal, wherein tissue comprises any cellular component of an animal. For example and without limitation, tissue can be derived from aggregates of cells, an organ, portions of an organ, or combinations of organs. In certain embodiments, the ECM is isolated from a vertebrate animal, for example and without limitation, human, monkey, pig, cattle, and sheep. In certain embodiments, the ECM is isolated from any tissue of an animal, for example and without limitation, urinary bladder, liver, CNS, adipose tissue, small intestine, large intestine, colon, esophagus, pancreas, dermis, and heart. In one embodiment, the ECM is derived from a urinary bladder. The ECM may or may not include the basement membrane portion of the ECM. In certain embodiments, the ECM includes at least a portion of the basement membrane. The ECM may or may not retain some of the cellular elements that comprised the original tissue such as capillary endothelial cells or fibrocytes.

As used herein, the term "derive" and any other word forms of cognates thereof, such as, without limitation, "derived" and "derives", refers to a component or components obtained from any stated source by any useful method. For example and without limitation, an ECM-derived gel refers to a gel comprised of components of ECM obtained from any tissue by any number of methods known in the art for isolating ECM. In another example, mammalian tissue-derived ECM refers to ECM comprised of components of mammalian tissue obtained from a mammal by any useful method.

Following isolation of the tissue of interest, decellularization is performed by various methods, for example and without limitation, exposure to hypertonic saline, peracetic acid, Triton-X or other detergents. Decellularized ECM can then be dried, either lyophilized (freeze-dried) or air dried. Dried ECM can be comminuted by methods including, but not limited to, tearing, milling, cutting, grinding, and shearing. The comminuted ECM can also be further processed into a powdered form by methods, for example and without limitation, such as grinding or milling in a frozen or freeze-dried state.

As used herein, the term "comminute" and any other word forms or cognates thereof, such as, without limitation, "comminution" and "comminuting", refers to the process of reducing larger particles into smaller particles, including, without limitation, by grinding, blending, shredding, slicing, milling, cutting, shredding. ECM can be comminuted while in any form, including, but not limited to, hydrated forms, frozen, air-dried, lyophilized, powdered, sheet-form.

In order to prepare solubilized ECM tissue, comminuted ECM is digested with an acid protease in an acidic solution to form a digest solution. As used herein, the term "acid protease" refers to an enzyme that cleaves peptide bonds, wherein the enzyme has increased activity of cleaving peptide bonds in an acidic pH. For example and without limitation, acid proteases can include pepsin and trypsin.

The digest solution of ECM typically is kept at a constant stir for a certain amount of time at room temperature. The ECM digest can be used immediately or be stored at $-20°$ C. or frozen at, for example and without limitation, $-20°$ C. or $-80°$ C., and in the context of the methods and compositions described herein, dried and sterilized. Next, the pH of the digest solution is raised to a pH between 7.2 and 7.8 to produce a neutralized digest solution. The pH can be raised by adding one or more of a base or an isotonic buffered solution, for example and without limitation, NaOH or PBS at pH 7.4. The method typically does not include a dialysis step prior to gelation, yielding a more-complete ECM-like matrix that typically gels at $37°$ C. more slowly than comparable collagen or dialyzed ECM preparations. The gel is therefore more amenable to injection into a patient, and also retains more of the qualities of native ECM due to retention of many native soluble factors, such as, without limitation, cytokines. The ability of non-dialyzed (whole ECM) preparations prepared from a variety of tissues to gel with kinetics suitable for use in molds or in situ is unexpected.

As used herein, the term "isotonic buffered solution" refers to an isotonic solution that is buffered to a pH between 7.2 and 7.8 and that has a balanced concentration of salts to promote an isotonic environment. As used herein, the term "base" refers to any compound or a solution of a compound with a pH greater than 7. For example and without limitation, the base is an alkaline hydroxide or an aqueous solution of an alkaline hydroxide. In certain embodiments, the base is NaOH or NaOH in PBS.

This neutralized digest solution can, at that point be incubated at a suitably warm temperature, for example and without limitation, at about $37°$ C. to gel. The neutralized digest solution can be frozen and stored at, for example and without limitation, $-20°$ C. or $-80°$ C. As used herein, the term "neutralized digest solution" or "neutralized digest" refers to a digest or digest solution wherein the pH is increased, and can be in the form of a solution or dried composition. For example and without limitation, a neutralized digest has a pH between 7.2 and 7.8.

Any type of extracellular matrix tissue can be used in the methods, compositions and devices as described herein (see generally, U.S. Pat. Nos. 4,902,508; 4,956,178; 5,281,422; 5,352,463; 5,372,821; 5,554,389; 5,573,784; 5,645,860; 5,711,969; 5,753,267; 5,762,966; 5,866,414; 6,099,567; 6,485,723; 6,576,265; 6,579,538; 6,696,270; 6,783,776; 6,793,939; 6,849,273; 6,852,339; 6,861,074; 6,887,495; 6,890,562; 6,890,563; 6,890,564; and 6,893,666), so long as the material is not terminally sterilized. In certain embodiments, the ECM is isolated from a vertebrate animal, for example and without limitation, from a warm blooded mammalian vertebrate animal including, but not limited to, human, monkey, pig, cow and sheep. The ECM can be derived from any organ or tissue, including without limitation, urinary bladder, intestine, liver, esophagus and dermis. In one embodiment, the ECM is isolated from a urinary bladder. In another embodiment, the ECM is isolated from intestine, or a portion thereof. The intestine extends from the pyloric sphincter to the anus, and includes: the small intestine, extending from the pyloric valve to the ileocecal valve; the large intestine, extending from the ileocecal valve; and portions thereof, including: the duodenum; the jejunum; the ileum; the cecum; the appendix; the ascending, transverse, descending and sigmoid colon; the rectum and/or the anal canal (See, e.g., Marieb, E N, *Human Anatomy and Physiology*, Second Edition, 1992, The Benjamin/Cummings Publishing Company, Inc., Redwood City, Calif., pp. 792, 793, 802, and 803). The ECM may or may not include the basement membrane portion of the ECM. In certain embodiments, the ECM includes at least a portion of the basement membrane.

The type of ECM used in the scaffold can vary depending on the intended cell types to be recruited during wound healing or tissue regeneration, the native tissue architecture of the tissue organ to be replaced, the availability of the tissue source of ECM, or other factors that affect the quality of the final scaffold and the possibility of manufacturing the scaffold. For example and without limitation, the ECM may contain both a basement membrane surface and a non-basement membrane surface, which would be useful for promoting the reconstruction of tissue such as the urinary bladder, esophagus, or blood vessel all of which have a basement membrane and non-basement membrane component.

Figure 3:
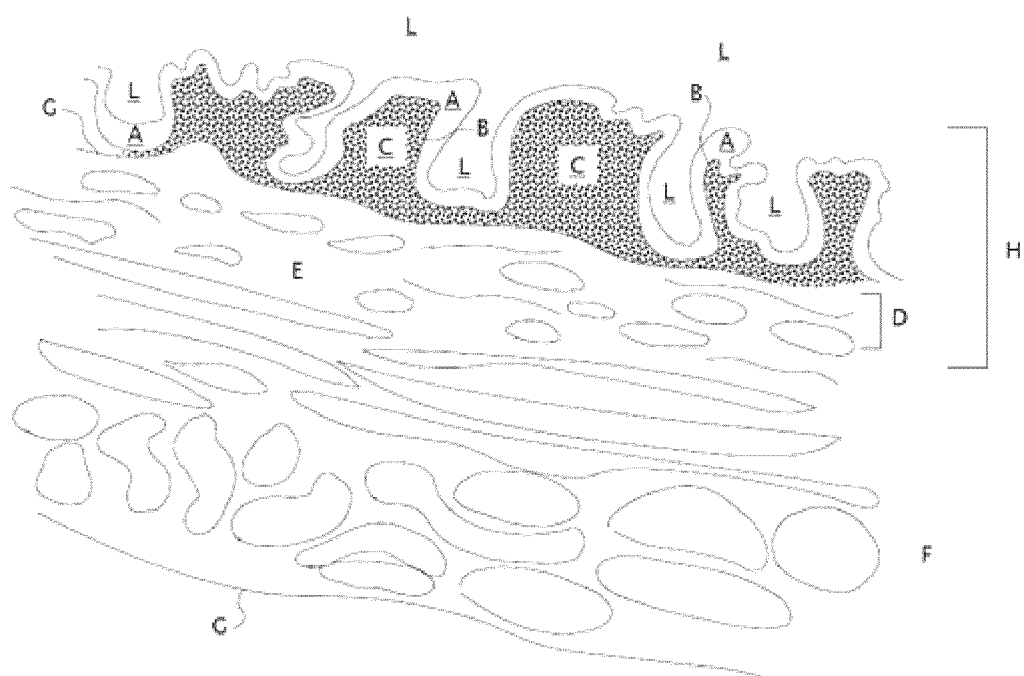
FIG. 3 is a schematic of a cross-sectional view of the wall of the urinary bladder (not drawn to scale). The following structures are shown: epithelial cell layer (A), basement membrane (B), tunica propria (C), muscularis mucosa (D), tunica submucosa (E), tunica muscularis externa (F), tunica serosa (G), tunica mucosa (H), and the lumen of the bladder (L).

In one non-limiting embodiment, the ECM is harvested from porcine urinary bladders (also known as urinary bladder matrix or UBM). Briefly, the ECM is prepared by removing the urinary bladder tissue from a pig and trimming residual external connective tissues, including adipose tissue. All residual urine is removed by repeated washes with tap water. The tissue is delaminated by first soaking the tissue in a deepithelializing solution, for example and without limitation, hypertonic saline (e.g. 1.0 N saline), for periods of time ranging from ten minutes to four hours. Exposure to hypertonic saline solution removes the epithelial cells from the underlying basement membrane. Optionally, a calcium chelating agent may be added to the saline solution. The tissue remaining after the initial delamination procedure includes the epithelial basement membrane and tissue layers abluminal to the epithelial basement membrane. This tissue is next subjected to further treatment to remove most of the abluminal tissues but maintain the epithelial basement membrane and the tunica propria. The outer serosal, adventitial, tunica muscularis mucosa, tunica submucosa and most of the muscularis mucosa are removed from the remaining deepithelialized tissue by mechanical abrasion or by a combination of enzymatic treatment (e.g., using trypsin or collagenase) followed by hydration, and abrasion. Mechanical removal of these tissues is accomplished by removal of mesenteric tissues with, for example and without limitation, Adson-Brown forceps and Metzenbaum scissors and wiping away the tunica muscularis and tunica submucosa using a longitudinal wiping motion with a scalpel handle or other rigid object wrapped in moistened gauze. Automated robotic procedures involving cutting blades, lasers and other methods of tissue separation are also contemplated. After these tissues are removed, the resulting ECM consists mainly of epithelial basement membrane and subjacent tunica propria (layers B and C of FIG. 3).

In another embodiment, the ECM is prepared by abrading porcine bladder tissue to remove the outer layers including both the tunica serosa and the tunica muscularis (layers G and F in FIG. 3) using a longitudinal wiping motion with a scalpel handle and moistened gauze. Following eversion of the tissue segment, the luminal portion of the tunica mucosa (layer H in FIG. 3) is delaminated from the underlying tissue using the same wiping motion. Care is taken to prevent perforation of the submucosa (layer E of FIG. 3). After these tissues are removed, the resulting ECM consists mainly of the tunica submucosa (layer E of FIG. 3).

A large number of ECM preparations are commercially available, prepared by numerous processes. Commercially available small intestinal submucosa (SIS) preparations include, but are not limited to, Surgisis™, Surgisis-ES™, Stratasis™, and Stratasis-ES™ (Cook Urological Inc.; Indianapolis, Ind.) and GraftPatch™ (Organogenesis Inc.; Canton Mass.). Commercially available dermis preparations include, but are not limited to Pelvicol™ (sold as Permacol™ in Europe; Bard, Covington, Ga.), Repliform™ (Microvasive; Boston, Mass.) and Alloderm™ (LifeCell; Branchburg, N.J.). Commercially available urinary bladder preparations include, but are not limited to UBM (Acell Corporation; Jessup, Md.). Any of these ECM preparations can potentially be provided in a form that is not terminally sterilized, and thus can be a suitable precursor for the methods and compositions described herein.

The compositions described herein can be used in a number of ways or forms. For example and without limitation, according to a first embodiment, the neutralized digest is placed in a suitable mold to model an organ or a portion thereof. As a non-limiting example, the composition is molded into a portion of a liver to facilitate re-growth of liver tissue. In another non-limiting example, the composition is molded in the shape of nose or ear cartilage, or a portion thereof, for replacement of damaged or excised cartilaginous tissue. In yet another non-limiting example, the composition is molded into the shape of a wound to facilitate non-scarring healing of that tissue. To prepare the molded gel, the neutralized digest is placed in a biocompatible and preferably sterile mold, such as a plastic mold, and is incubated at a temperature and for a time suitable for gelation of the composition, for example and without limitation at about 37° C. In one embodiment, the composition and mold is placed in an incubator at 37° C. to gel. Because $CO_2$ has been found to slow gelation, in one non-limiting embodiment, $CO_2$ is not injected into the incubator, though in yet another embodiment, $CO_2$ and/or temperature may be used to control the gelation process.

Any useful cytokine, chemoattractant or cells can be mixed into the composition prior to gelation or diffused, absorbed and/or adsorbed by the gel after it is gelled. For example and without limitation, useful components include growth factors, interferons, interleukins, chemokines, monokines, hormones, angiogenic factors, drugs and antibiotics. Cells can be mixed into the neutralized, solubilized gel or can be placed atop the molded composition once it is gelled. In either case, when the gel is seeded with cells, the cells can be grown and/or adapted to the niche created by the molded ECM gel by incubation in a suitable medium in a bioreactor or incubator for a suitable time period to optimally/favorably prepare the composition for implantation in a patient. The molded composition can be seeded with cells to facilitate in-growth, differentiation and/or adaptation of the cells. For example and without limitation, the cells can be autologous or allogeneic with respect to the patient to receive the composition/device comprising the gel. The cells can be stem cells or other progenitor cells, or differentiated cells. In one example, a layer of dermis obtained from the patient is seeded on a mold, for use in repairing damaged skin and/or underlying tissue.

As used herein, the term "mold" refers to a cavity or surface used to form the gel into a three-dimensional shape. For example and without limitation, the mold can be a well plate, cell culture dish or a tube or can be shaped into any useful shape. In a certain embodiment, the mold can be shaped into a certain organ or part of an organ. The gel can be delivered to the mold in a variety of methods, including, but not limited to, injection, deposition.

As used herein, the terms "drug" and "drugs" refer to any compositions having a preventative or therapeutic effect, including and without limitation, antibiotics, peptides, hormones, organic molecules, vitamins, supplements, factors, proteins and chemoattractants.

As used herein, the terms "cell" and "cells" refer to any types of cells from any animal, such as, without limitation, rat, mice, monkey, and human. For example and without limitation, cells can be progenitor cells, such as stem cells, or differentiated cells, such as endothelial cells, smooth muscle cells. In certain embodiments, cells for medical procedures can be obtained from the patient for autologous procedures or from other donors for allogeneic procedures.

One favorable aspect of the use of pre-molded tissue is that a layered composition can be produced. For example, a core portion of the composition to be implanted can be prepared with a first ECM gel, obtained from a first source, and a surrounding layer can be with a second ECM gel, obtained from a second source different from the first, or the same source as the first, but containing different constituents, such as cytokines or cells.

In another embodiment of the pre-molded composition, the ECM gel is contained within a laminar sheath of non-comminuted and non-digested ECM tissue, such as SIS or UBM, to add physical strength to the gel. In this embodiment, sheets of ECM tissue, prepared in any manner known in the art, can be placed into the mold prior to filling the mold with the solubilized ECM tissue for producing the gel. The sheets of ECM tissue may be used as the mold, so long as they are formed and sewn or cross-linked into a desired shape. In this manner, a solid composition can be produced that has greater physical strength than is the case of a gel, alone.

In another non-limiting embodiment, the composition is injected as a neutralized digest solution into a patient. The composition is injected at a locus in the patient where the matrix is needed for cell growth. For example and without limitation, where a patient has had tissue removed due to trauma, debridement and/or removal of damaged, diseased or cancerous tissue, the composition can be injected at the site of tissue removal to facilitate in-growth of tissue. The viscosity of the pre-gel can be controlled by varying the amounts of water (e.g., by varying the amounts of water, acid, base, buffer (such as PBS) or other diluents) used to prepare the pre-gel. In applications in which a small gauge needle is used, such as in endoscopy, a less viscous pre-gel would be needed, which typically results in a less viscous gel, once the pre-gel is gelled. In applications in which a larger gauge needle is available, a more viscous gel, with higher strength when gelled, can be used. Also, use of a larger gauge needle, irrespective of the viscosity of the pre-gel, favors mixing of live cells with the pre-gel immediately prior to implantation with less risk of shearing the cells.

In one embodiment, a neutralized digest solution is prepared by raising the pH of the acidic digest solution and the composition is directly injected into a patient prior to significant gelation proceeds. In one embodiment, the composition is in a frozen state and is thawed and warmed prior to injection. In another embodiment, the acidic digest solution is warmed to physiological temperature and is mixed during injection in a static mixer with suitable quantities of a base and/or buffer, such as PBS. Suitable static mixers include, without limitation, helical or square static mixers, commercially available from Cammda Corporation of Cobourg, Ontario, Canada or a Mini-Dual Syringe with Micro Static Mixer commercially available from Plas-Pak Industries, Inc. of Norwich, Conn.

In a further embodiment, a commercial kit is provided comprising a composition described herein. A kit comprises suitable packaging material and the composition. In one non-limiting embodiment, the kit comprises a digest solution in a vessel, which may be the packaging, or which may be contained within packaging. In this embodiment, if the digest solution is neutralized, it may be frozen, cooled; e.g., kept at near-freezing temperatures, such as, without limitation, below about 4° C. or kept at room temperature, e.g., 20-25° C. In another non-limiting embodiment, the kit comprises a first vessel containing an acidic solution comprising a pre-neutralization digest as described herein, and a second vessel comprising a neutralizing solution comprising a base and/or buffer(s) to bring the acidic solution of the first vessel to physiological ionic strength and pH, to form a neutralized digest. In a further embodiment, the first vessel contains a terminally sterilized, lyophilized, pre-neutralization digest that can be hydrated using water or a suitable aqueous solution that optionally neutralizes the acid. In this embodiment, a second vessel is optionally provided comprising a neutralization solution as described above that is capable of both hydrating the lyophilized product and neutralizing it, or optionally a third vessel comprising water or any other suitable solution useful in hydrating the lyophilized product prior to neutralization with the neutralization solution. This kit also optionally comprises a mixing needle and/or a cold-pack. The vessel may be a vial, syringe, tube or any other container suitable for storage and transfer in commercial distribution routes of the kit.

In yet another embodiment of the kit, gel composition is molded and pre-gelled prior to packaging and distribution. In one embodiment, the molded gel is packaged in a blister-pack comprising a plastic container and a paper, plastic and/or foil sealing portion, as are well-known in the art. The mold and packaging typically is sterilized prior to or after packaging, for example and without limitation, by gamma or electron beam irradiation or supercritical $CO_2$. The molded composition may be packaged in any suitable physiological solution, such as PBS or saline. If the molded gel contains live cells, the mold can be transported in a suitable cell-culture medium in a sealed jar or other vessel. Of course, the cell-containing molded gel would have to be shipped in an expedited manner to preserve the cells.

As used herein, the term "hybrid inorganic/ECM scaffold" refers to an ECM-derived gel that is coated onto a biocompatible inorganic structure, such as, without limitation, a metal, an inorganic calcium compound such as calcium hydroxide, calcium phosphate or calcium carbonate, or a ceramic composition. In one embodiment, ultrasonication is used to aid in coating of the inorganic structure with the ECM-derived gel. As used herein, the term "ultrasonication" refers to the process of exposing ultrasonic waves with a frequency higher than 15 kHz and lower than 400 kHz.

As used herein, the term "coat", and related cognates such as "coated" and "coating," refers to a process comprising of covering an inorganic structure with ECM-derived gel or hybrid inorganic/ECM scaffold. For example and without limitation, coating of an inorganic structure with ECM-derived gel can include methods such as pouring, embedding, layering, dipping, spraying.

In another embodiment of the technology described herein, the composition is coated onto a biocompatible structural material, such as a metal, an inorganic calcium compound such as calcium hydroxide, calcium phosphate or calcium carbonate, or a ceramic composition. Non-limiting examples of suitable metals are cobalt-chrome alloys, stainless steel alloys, titanium alloys, tantalum alloys, titanium-tantalum alloys, which can include both non-metallic and metallic components, such as molybdenum, tantalum, niobium, zirconium, iron, manganese, chromium, cobalt, nickel aluminum and lanthanum, including without limitation, CP Ti (commercially pure titanium) of various grades or Ti 6Al 4V (90% wt. Ti, 6% wt. Al and 4% wt. V), stainless steel 316, Nitinol (Nickel-titanium alloy), titanium alloys coated with hydroxyapatite. Metals are useful due to high strength, flexibility, and biocompatibility. Metals also can be formed into complex shapes and many can withstand corrosion in the biological environments, reduce wear, and not cause damage to tissues. In one non-limiting example, the metal is femoral or acetabular component used for hip repair. In another example, the metal is a fiber or other protuberance used in permanent attachment of a prosthesis to a patient. Other compositions, including ceramics, calcium compounds, such as, without limitation, aragonite, may be preferred, for example and without limitation, in repair of or re-shaping of skeletal or dental structures. Combinations of metal, ceramics and/or other materials also may prove useful. For instance, a metal femoral component of a hip replacement may comprise a ceramic ball and/or may comprise a plastic coating on the ball surface, as might an acetabular component.

Metals, as well as other materials, as is appropriate, can be useful in its different forms, including but not limited to wires, foils, beads, rods and powders, including nanocrystalline powder. The composition and surface of metals or other materials can also be altered to ensure biocompatibility, such as surface passivation through silane treatments, coating with biocompatible plastics or ceramics, composite metal/ceramic materials. The materials and methods for their employment are well-known in the field of the present invention.

A difficulty with using metal inserts to repair a patient's skeletal structure is that the inserts must be anchored/attached to existing skeletal parts. Traditional methods employ cement and/or screws. In the case of prostheses, the prostheses are not connected to a patient's tissue except, typically, by cementing. Therefore, it is desirable to biologically attach a patient's tissue to a medical device. This may be accomplished by coating surfaces of the implant with the ECM gel described herein, which will facilitate in-growth of tissue and thus attachment of the device. A variety of porous structures can be attached to the implant to create a scaffold into which the ECM gel, and later cells or other tissue (e.g., bone) can infiltrate. Structures include, without limitation: woven or non-woven mesh, sponge-like porous materials, fused beads, etc. The porous scaffold will facilitate formation of a strong bond between living tissue, including bone, and the device. The "pores" of the porous scaffold may be of any size that will permit infiltration of an ECM gel, optionally facilitated by ultrasound or other treatments that would assist in permeation of the gel, and later cells or other biological materials, such as bone, cartilage, tendons, ligaments, fascia or other connective tissue, into the scaffolding. In one embodiment, metal fibers are attached to the device, and the metal fibers are coated with an ECM gel described herein, thereby permitting in-growth of tissue within the fibers. In a second embodiment, a matrix of small beads is welded or otherwise attached to a surface of the device and an ECM gel described herein is coated onto the bead matrix, facilitating in-growth of tissue among the beads. In one example, a device contains a protuberance of fibers, which can be inserted inside a bone, permitting fusion of the metal fibers with the bone. In one embodiment, the ECM gel is seeded and incubated with a suitable cell population, such as autologous osteoblasts, to facilitate bone in-growth.

In another embodiment, the hybrid inorganic/ECM scaffold can also be used to coat other structural implants, such as, without limitation, a femoral implant, a prosthesis of the hand. FIG. 1 shows schematically one embodiment of a device 10 inserted into a femur 15 in a hip replacement procedure. FIG. 1 illustrates device 10, showing an insert portion 20 for insertion into femur 15, and an extension 25 into which a ball (not shown) is screwed or otherwise inserted. Device 10 comprises a porous coating 30 of, for example and without limitation, metal beads welded onto the device 10. Region A in FIG. 1 shows a magnified view of coating 30 of device 10. Beads 32 are welded to metal surface 34 of device 10. ECM gel 36 is coated onto and between beads 32. Bone tissue growth into beads 32 is facilitated by the presence of the ECM gel 36.

Figure 2:
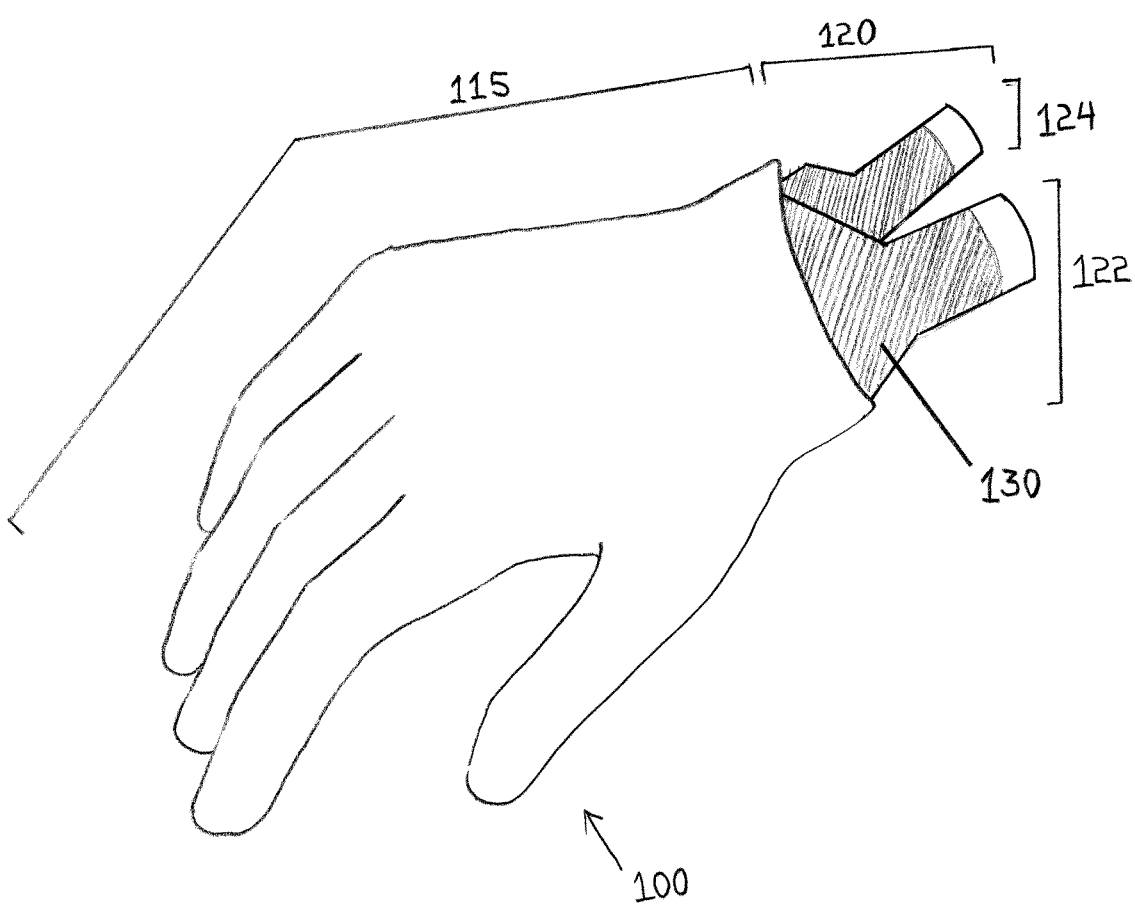
FIG. 2 shows schematically one embodiment of a hand prosthesis described herein.

A prosthesis might be anchored into bone in a like manner using an insert having a porous coating, with the porous coating extending to the limits of where attachment to a patient's tissue is desired. As an example, shown in FIG. 2, a hand prosthesis 100 comprises an external portion 115 and an internal portion 120, which comprises a radius insert portion 122 and an ulnar insert portion 124. Porous coating 130 extends from insert portions 122 and 124 for attachment to bone, to the beginning of external portion 115, permitting attachment of dermis and intermediary tissue between the bones and dermis.

A device (e.g., a prosthesis) as described herein can be coated with neutralized pre-gel and the temperature of the gel is then raised to cause the neutralized pre-gel to gel. In another embodiment, the acidic pre-gel is applied to the device or prostheses. The pre-gel on the device can then be dried, e.g. lyophilized and the entire device can be terminally sterilized, followed by packaging and distribution. The lyophilized product on the device can be hydrated by an end-user, and neutralized by application of water, saline or PBS to the device, and subsequently or concurrently raising the temperature of the device, e.g., above 37° C.

In use, the device which is coated with a suitable scaffolding and ECM gel as described herein may be contacted with cells, e.g. of a patient or allogeneic cells, and the cells are allowed to infiltrate the matrix. The in-growth or infiltration of cells can occur in vivo or ex vivo, depending on optimization of methods. For example and without limitation, in the case of a femoral implant, the implant can be inserted into the femur and cells of a patient, and desirable bone tissue, infiltrates the scaffolding to fuse the device to the bone. In another embodiment, for example in the case of an artificial tendon or ligament, a biopsy of a patient's tendons or ligaments is incubated with an appropriate scaffold in order to create an autologous ligament or tendon graft.

EXAMPLES

Example 1—Preparation of Porcine Extracellular Matrix (ECM) (UBM)

The preparation of UBM has been previously described [Sarikaya A, et al. Tissue Eng. 2002 February; 8(1):63-71; Ringel R L, et al. J Speech Lang Hear Res. 2006 February; 49(1):194-208]. In brief, porcine urinary bladders were harvested from 6-month-old 108-118 kg pigs (Whiteshire-Hamroc, Ind.) immediately following euthanasia. Connective tissue and adipose tissue were removed from the serosal surface and any residual urine was removed by repeated washes with tap water. The tunica serosa, tunica muscularis externa, the tunica submucosa, and majority of the tunica muscularis mucosa were mechanically removed. The urothelial cells of the tunica mucosa were dissociated from the luminal surface by soaking the tissue in 1.0 N saline solution yielding a biomaterial composed of the basement membrane plus the subjacent tunica propria, which is referred to as urinary bladder matrix (UBM). See FIG. 3 for cross-sectional view of the wall of the urinary bladder, as well as structures included within.

Figure 4A:
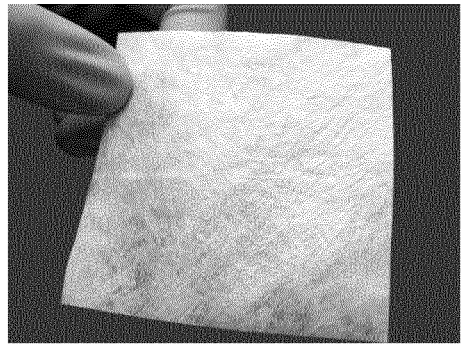
FIG. 4A is a photograph of lyophilized porcine urinary bladder matrix (UBM) sheet.
Figure 4B:
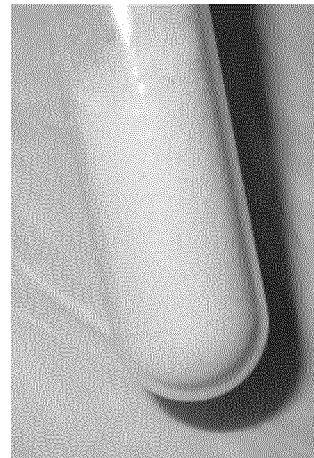
FIG. 4B is a photograph of lyophilized porcine urinary bladder matrix (UBM) powder.

The UBM sheets were disinfected for two hours on a shaker in a solution containing 0.1% (v/v) peracetic acid, 4% (v/v) ethanol, and 95.9% (v/v) sterile water. The peracetic acid residue was removed by washing with sterile phosphate-buffered saline (pH=7.4) twice for 15 minutes each and twice for 15 minutes each with sterile water. The UBM sheets (as in FIG. 4A) were then lyophilized (FIG. 4B) using a FTS Systems Bulk Freeze Dryer Model 8-54 and powdered using a Wiley Mini Mill.

Figure 4C:
FIG. 4C is a photograph of pepsin-digested solution at a concentration of 10 mg/ml of UBM.

One gram of lyophilized UBM powder (FIG. 4B) and 100 mg of pepsin were both mixed in 100 ml of 0.01 M HCl. The solution was kept at a constant stir for ~48 hrs at room temperature (25° C.). After pepsin digestion, the digest solution (FIG. 4C) was aliquoted and stored at −20° C. until use. After completion, the solution is referred to as digest solution or ECM digest or ECM stock solution.

Example 2—Preparation of Porcine Spleen ECM

Fresh spleen tissue was obtained. Outer layers of the spleen membrane were removed by slicing, where remaining tissue was cut into uniform pieces. Remnants of outer membrane were trimmed, then rinsed three times in water. Water was strained by using a sieve. Splenocytes were lysed by massaging. Spleen slices were incubated in a solution of 0.02% trypsin/0.05% EDTA at 37° C. for 1 hour in a water bath. If necessary, splenocytes were further lysed by massaging. After rinsing, slices were soaked in 3% Triton X-100 solution and put on a shaker for 1 hour. If necessary, splenocytes were further lysed by massaging. Slices were then soaked in 4% deoxycholic acid solution and put on a shaker for 1 hour. After thoroughly rinsing, the purified spleen ECM was stored for further processing. This tissue was next disinfected with peracetic acid treatment and dried.

One gram of dry porcine spleen ECM and 100 mg of pepsin were both mixed in 100 ml of 0.01 M HCl. The solution was kept at a constant stir for ~72 hrs at room temperature (25° C.). If there are no visible pieces of the ECM floating in the solution, aliquot the sample and freeze (−20° C.) or use immediately.

Example 3—Preparation of Porcine Liver Stroma ECM

Fresh liver tissue was obtained. Excess fat and tissue were trimmed. Outer layers of the liver membrane were removed by slicing, where remaining tissue was cut into uniform pieces. Remnants of outer membrane were trimmed using a scalpel or razor blade, then rinsed three times in water. Water was strained by using a sieve. Cells were lysed by massaging. Liver slices were incubated in a solution of 0.02% trypsin/0.05% EDTA at 37° C. for 1 hour in a water bath. If necessary, cells were further lysed by massaging. After rinsing, slices were soaked in 3% Triton X-100 solution and put on a shaker for 1 hour. If necessary, cells were further lysed by massaging. Slices were then soaked in 4% deoxycholic acid solution and put on a shaker for 1 hour. After thoroughly rinsing, the purified liver stroma was stored in deionized water for further processing. This tissue was next disinfected with peracetic acid treatment and dried.

One gram of dry porcine liver stroma ECM and 100 mg of pepsin were both mixed in 100 ml of 0.01 M HCl. The solution was kept at a constant stir for ~24-48 hrs. at room temperature (25° C.). If there are no visible pieces of the ECM floating in the solution, aliquot the sample and freeze (−20° C.) or use immediately.

Example 4—Preparation of Human Liver Stroma ECM

Fresh liver tissue was obtained. Excess fat and tissue were trimmed. Outer layers of the liver membrane were removed by slicing, where remaining tissue was cut into uniform pieces. Remnants of outer membrane were trimmed using a scalpel or razor blade, then rinsed three times in water. Water was strained by using a sieve. Cells were lysed by massaging. Liver slices were incubated in a solution of 0.02% trypsin/0.05% EDTA at 37° C. for 1 hour in a water bath. If necessary, cells were further lysed by massaging. After rinsing, slices were soaked in 3% Triton X-100 solution and put on a shaker for 1 hour. If necessary, cells were further lysed by massaging. Slices were then soaked in 4% deoxycholic acid solution and put on a shaker for 1 hour. After thoroughly rinsing, the purified liver stroma was stored in deionized water for further processing. This tissue was next disinfected with peracetic acid treatment and dried.

One gram of dry human liver stroma ECM and 200 mg of pepsin were both mixed in 50 ml of 0.01 M HCl. The solution was kept at a constant stir for ~3-5 days at room temperature (25° C.). The solution will need to be monitored every day. If there are no visible pieces of the ECM floating in the solution, aliquot the sample and freeze (−20° C.) or use immediately.

Example 5—Preparation of Porcine Cardiac ECM

One gram of dry porcine cardiac ECM with 100 mg of pepsin were both mixed in 50 mL of 0.01 M HCl. The solution was kept at a constant stir for ~48 hours at room temperature (25° C.).

Example 6—Preparation of Porcine Pancreatic ECM

One gram of dry de-fatted porcine pancreatic ECM with 100 mg of pepsin were both mixed in 50 mL of 0.01 M HCl. The solution was kept at a constant stir for ~48 hours at room temperature (25° C.).

Example 7—Preparation of Porcine Ovarian ECM

Fresh ovarian tissue is obtained within 6 hours of harvest. Ovaries were removed and stored in physiological saline tissue until ready for dissection and residual uterine tissue was removed. Longitudinal incisions were made through the hilum of the ovary and the follicles were disrupted. Once all the follicles have been disrupted, the ECM has been harvested from the ovaries. Rinse three times in filtered water and strain the water using a sieve. Cells were lysed by gentle massaging. ECM was incubated in a solution of 0.02% trypsin/0.05% EDTA at 37° C. for 1 hour in a water bath and then rinsed. If necessary, cells were further lysed by massaging. ECM was soaked in 3% Triton X-100 solution and put on a shaker for 1 hour. After rinsing, cells were further lysed by massaging if necessary. Slices were then soaked in 4% deoxycholic acid solution and put on a shaker for 1 hour. After thoroughly rinsing to remove residual surfactant, the ECM was stored in sterile/filtered water until further use. This tissue was next disinfected with peracetic acid treatment and dried.

One gram of lyophilized ovarian ECM powder and 100 mg of pepsin were both mixed in 100 ml of 0.01 M HCl. The solution was kept at a constant stir for ~48 hrs at room temperature (25° C.). After pepsin digestion, the digest solution was aliquoted and stored at −20° C. until use.

Example 8: Preparation of Spinal Cord and Dura Mater ECM

Using forceps, scissors and a scalpel, dura mater was removed from porcine spinal cord. The inner dura mater surface was scrapped with scalpel blade to remove any debris. The spinal cord and dura were placed in separate containers and treated in the same manner as below. The spinal cord was cut either longitudinally or in cross-section to increase surface area and placed in a cassette. Optionally tissue was enzymatically treated using trypsin-EDTA for 30 minutes at 37° C. The tissue was incubated in Triton X-100™ (4-octylphenol polyethoxylate) solutions at 3% for periods up to 2-3 days at 4° C. This step was repeated with a solution of Triton X100™ at 6% and again with a solution of Triton X100™ at 9%. The spinal cord tissue was incubated in lecithin or lecithin-deoxycholate to remove lipids overnight at 4° C. Dura mater was not subjected to this procedure. Tissue was then washed in Triton X100™ 3% or SDS 1% for 1-2 hours. The tissue was rinsed in PBS 3× for 15 minutes at room temperature. Then the tissue was incubated in a solution of DNase I for 1 hour at room temperature. The tissue was washed in PBS three times for 15 minutes at room temperature. Lastly, the tissue was washed in deionized water three times for 15 minutes at room temperature. The procedure produced a gel-like acellular spinal cord material, and a sheet of acellular dura mater material.

Example 9—Preparation of Adipose ECM

Frozen adipose tissue was thawed in water and manually massaged to hasten the lysis of cells. Tissue was placed into a flask containing 0.02% trypsin/0.05% EDTA solution and incubated at 37° C. for one hour then rinsed briefly in distilled deionized water (ddH$_2$O) and manually massaged again. Tissue was then placed into a flask containing 3% Triton X-100 and placed on an orbital shaker for 1 hour at room temperature. Following a brief water rinse, tissue was placed into a 4% deoxycholic acid solution and again placed on an orbital shaker for 1 hour at room temperature. Tissue was rinsed three times in water and stored at 4° C. overnight. The tissue was then subjected to a 4% ethanol and 0.1% peracetic acid solution on an orbital shaker for 2 hours at followed by two phosphate buffered saline (PBS, pH 7.4) and two water washes of 15 minutes each at room temperature. The resulting material was then washed in 100% n-propanol for one hour on an orbital shaker at room temperature and washed in four changes of ddH$_2$O for one hour to remove the n-propanol prior to lyophilization.

Example 10—Preparation of Neural-Derived ECM Gel

Murine spinal cord tissue was stored at −80° C. until needed for ECM derivation processing. The material was thawed and the dura mater was removed from the spinal cord, and the spinal cord was then cut into quarters longitudinally of about 1 inch length and uniform thickness. The spinal cord pieces were placed into water overnight at 4° C. and 120 rpm to mechanically-disrupt the native tissue architecture prior to decellularization. After about 18 h the spinal cord pieces were removed from the water by straining onto a mesh or sieve with hole size of about 840 µm. The pieces of spinal cord were collected with forceps and placed into a flask for protease digestion with 0.02% trypsin/0.05% EDTA solution. The digestion was allowed to proceed in a water bath for 1 h at 37° C. while shaking at 120 rpm. After one hour, the solution was strained off and spinal cord tissue was rinsed gently under a stream of water, detangling as required. The spinal cord pieces were returned to the flask, collecting as many smaller tissue pieces as possible from the strainer using forceps. 3% Triton X-100 solution was then added to the flask to begin decellularization of the tissue, which was placed on a shaker for 1 h at 200 rpm. After one hour the tissue was strained, rinsed, and collected. The tissue pieces were placed back into the flask, and then were subjected to osmotic shock for additional decellularization. Hypertonic 1 M sucrose was added to the flask and placed on a shaker for 15 min at 200 rpm. The tissue was strained, rinsed, collected and combined with hypotonic solution (deionized water) and placed on shaker for 15 min at 200 rpm, to lyse any remaining cells. The decellularized tissue was again strained, rinsed, and reclaimed into a flask. 4% deoxycholate solution was added to the flask and placed upon a shaker for 1 h at 200 rpm. Subsequently, the tissue pieces were strained and rinsed repeatedly in type I (ultrapure) water until all traces of surfactants (bubbles) were removed. The remaining tissue, now enriched into ECM, was collected and disinfected using a peracetic acid solution (made up of Type I water (96%) and 100% EtOH alcohol (4%)) at a ratio of 20:1 peracetic acid solution to weight of ECM, and shaken at 200 rpm for two hours. Following a series of rinse steps in Phosphate Buffered Saline (PBS), the ECM was frozen at −20° C. and then lyophilized until all water was removed. Gel scaffold pre-gel material was manufactured by adding lyophilized ECM into a 0.01 N hydrochloric acid solution containing 1.0 mg/ml pepsin, which is diluted with isotonic saline to yield ECM concentrations between about 1 mg/ml and 200 mg/ml depending upon the desired viscosity of the scaffold.

Example 11—General Method of Preparation of Gels from ECM

Figure 4D:
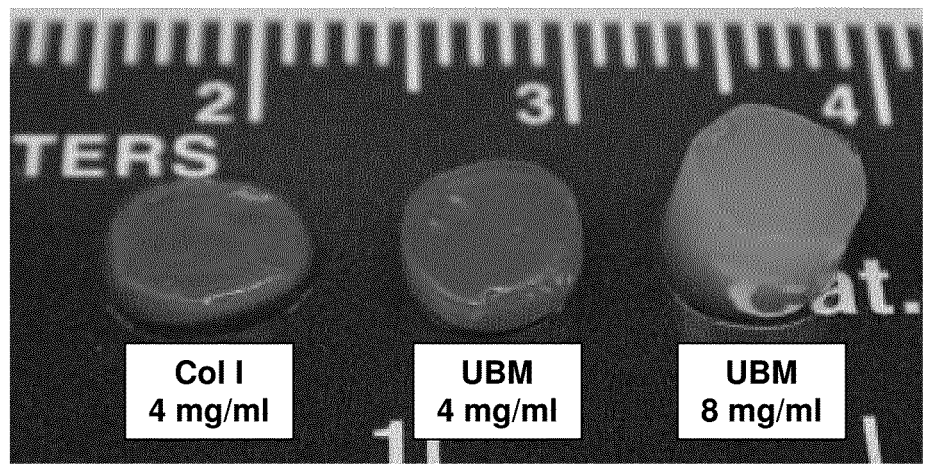
FIG. 4D is a photograph of gels at 4 mg/ml of UBM and at 8 mg/ml of UBM, where a gel of collagen I (Col I) at 4 mg/ml is shown for comparison (D).
Figure 6A:
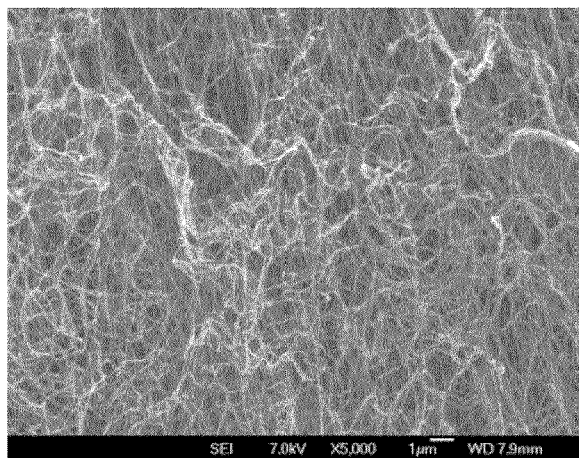
FIG. 6A is a scanning electron micrograph (SEM) image of 3 mg/ml UBM gel at 5,000×.
Figure 6B:
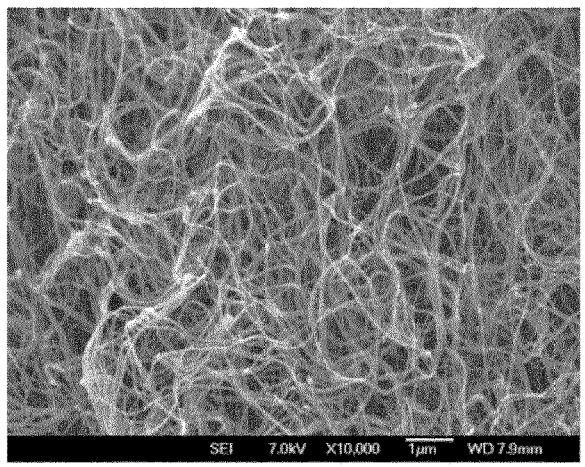
FIG. 6B is a scanning electron micrograph (SEM) image of 3 mg/ml UBM gel at 10,000×.
Figure 6C:
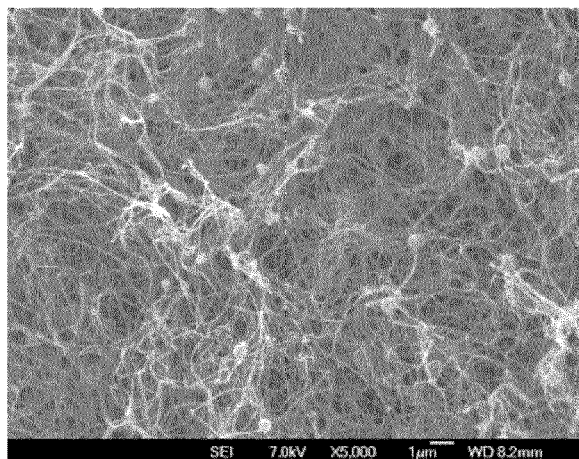
FIG. 6C is a scanning electron micrograph (SEM) image of 6 mg/ml UBM gel at 5,000×.
Figure 6D:
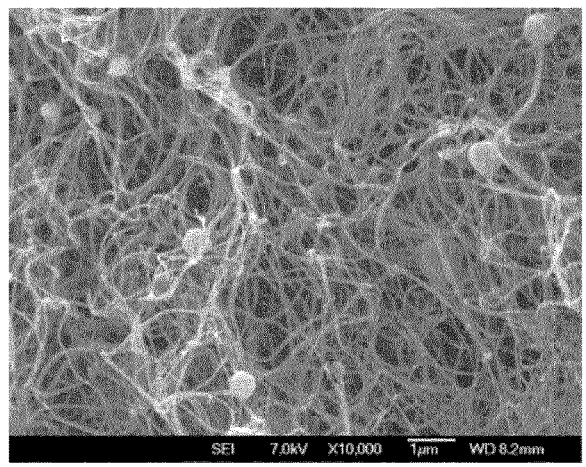
FIG. 6D is a scanning electron micrograph (SEM) image of 6 mg/ml UBM gel at 10,000×.

UBM gel was formed into a gel by mixing 0.1 N NaOH (1/10 of the volume of digest solution) and 10×PBS pH 7.4 (1/9 of the volume of digest solution) in appropriate amounts at 4° C. The solution was brought to the desired volume and concentration using cold (4° C.) 1×PBS pH 7.4 and placed in a 37° C. incubator for gelation to occur (FIG. 4D).

The ECM was able to form a matrix after 40 minutes in solution as shown in FIG. 4. The ECM-derived gel was liquid at temperatures below 20° C. but turn into a gel when the temperature is raised to 37° C.

In preparing gels from ECM, all of the following solutions should be kept on ice and the following variables must be determined:

$C_f$=concentration of the final gel in mg/ml
$C_s$=concentration of the ECM digest solution in mg/ml
$V_f$=volume of the final gel solution needed for the experiments
$V_d$=volume needed from the ECM digest solution in ml
$V_{10X}$=volume of 10×PBS needed in ml
$V_{1X}$=volume of 1×PBS needed in ml
$V_{NaOH}$=volume of 0.1 N NaOH needed in ml First, determine the final concentration ($C_f$) and volume ($V_d$) of ECM gel required. Then, calculate the mass of ECM needed by multiplying $C_f$ (mg/ml)*$V_f$ (ml) This value will give you the volume needed from the ECM digest solution ($V_d$), where $V_d$=[$C_f$ (mg/ml)*$V_f$ (ml)]/$C_s$.

Calculate the volume of 10×PBS needed by dividing the calculated volume $V_d$ by 9 ($V_{10X}=V_d/9$). Calculate the volume of 0.1 N NaOH needed by dividing the calculated volume $V_d$ by 10 ($V_{NaOH}=V_d/10$). Calculate the amount of 1×PBS needed to bring the solution to the appropriate concentration/volume as follow: $V_{1X}=V_f-V_d-V_{10X}-V_{NaOH}$. Add all the reagents ($V_{1X}+V_d+V_{10X}+V_{NaOH}$) to an appropriate container (usually 15 or 50 ml centrifuge tubes) without the ECM digest ($V_d$). Place solutions on ice and keep on ice at all times.

Add the appropriate volume from the ECM digest solution ($V_d$) to the PBS/NaOH mixture prepared above and mix well with a 1 ml micropipette while being careful and avoiding the creation of air bubbles in the solution. Depending on the viscosity of the ECM digest solution, there might be some significant volume loss during the transfer. Monitor the total volume and add appropriate amounts until the final volume is achieved. Measure the pH of the pre-gel solution, where pH should be around 7.4.

Add the pre-gel solution to a mold or to appropriate wells. Place the mold or wells in 37° C. incubator for a minimum of 40 minutes. Avoid using an incubator with $CO_2$ control. If water evaporation is a concern, place the mold inside a plastic zip-lock bag before placing in the incubator. After gelation, the gel can be removed from the mold and placed in 1×PBS. If the gels were made in tissue culture plates, 1×PBS can be placed on top of the gels until use to maintain the gels hydrated.

Sample calculation: Make 6 ml of gel with a final concentration of 6 mg/ml from the 10 mg/ml stock solution.

GIVEN: $C_s$=10 mg/ml; $C_f$=6 mg/ml; $V_f$=6 ml $V_d$=[6 mg/ml*6 ml]/10 mg/ml=3.600 ml $V_{10X}$=3.6/9=0.400 ml $V_{NaOH}$=3.6/10=0.360 ml $V_{1X}$=6 ml−3.6 ml−0.400 ml−0.360=1.640 ml

Example 12—Composition and Morphology of Porcine UBM

UBM and rat-tail collagen type I (BD, Biosciences) solutions were electrophoresed on 4-20% polyacrylamide gels under reducing conditions (5% 2-Mercaptoethanol). The proteins were visualized with Gel-Code Blue (Bio-Rad), and documented by a Kodak imaging station.

Collagen and sulfated glycosaminoglycan (S-GAG) content were determined using the hydroxyproline assay [Reddy G K, et al. "A simplified method for the analysis of hydroxyproline in biological tissues," (1996) Clin. Biochem. 29(3): 225-9] and the Blyscan™ assay kit (Biocolor, Northern Ireland) respectively (three samples were tested). The Blyscan™ assay was performed according to the manufacturer's instruction. The hydroxyproline content was determined by hydrolyzing the samples with 2 M NaOH (100 μl total volume) in an autoclave at 120° C. for 20 minutes. The samples were neutralized with 50 μl of 4 M HCl and reacted with 300 μl of 0.056 M chloramine-T (Spectrum), mixed gently, and allowed to oxidize for 25 minutes at room temperature. The samples were then mixed with 300 μl of 1 M Ehrlich's aldehyde (Spectrum) and incubated at 65° C. for 20 minutes. A standard curve was generated using rat-tail collagen type I (BD Biosciences) and used to calculate the total amount of collagen present in the digested UBM solutions. The colorimetric change was determined by the absorbance at 550 nm using a SpectraMax spectrophotometer.

The composition of the gel has been determined. The collagen concentration for pepsin digested UBM was found to be 0.8±0.2 mg per mg of dry lyophilized UBM powder (mean±SD). The total S-GAG content was found to be 5.1±0.9 μg per mg of dry lyophilized UBM powder (mean±SD). The electrophoresed proteins show the typical bands for collagen type I present on the UBM lane with extra bands as shown in FIG. 5. The difference may be in part due to the additional components, that is, to small peptides and glycosaminoglycans) present in the UBM gels.

The surface morphology of the UBM gels was examined using a scanning electron microscope (SEM). The specimens were fixed in cold 2.5% glutaraldehyde and rinsed in PBS, followed by a dehydration process through a graded series of ethanol (30% to 100%), and finally critically point dried in an Emscope CPD 750 critical point dryer. The samples were attached to aluminum SEM specimen mounting stubs (Electron Microscopy Sciences, Hatfield, Pa.) and sputter coated with a gold palladium alloy using a Sputter Coater 108 Auto (Cressington Scientific Instruments, Valencia, Pa.). Finally, samples were examined using a scanning electron microscope (JEOL 6330F). Images were taken at a 5,000 and 10,000× magnification. The scanning electron microscopy pictures show the fibrillar appearance of the UBM gels at concentrations of 3 mg/ml and 6 mg/ml (FIG. 6A-6D) as well as at 4 mg/ml (FIG. 7B).

Example 10—Rheological Properties and Gelation Kinetics of Porcine UBM, SIS and LS Gels The rheological properties of the UBM derived gel were characterized during gelation. The UBM gel consists of a viscous solution at temperature below 25° C. and a gel at physiological temperatures (37° C.). Rheological properties of other gels can be measured using similar methods described herein. Rheological properties of liver stroma (LS) and small intestine submucosa (SIS) were also measured.

Figure 8A:
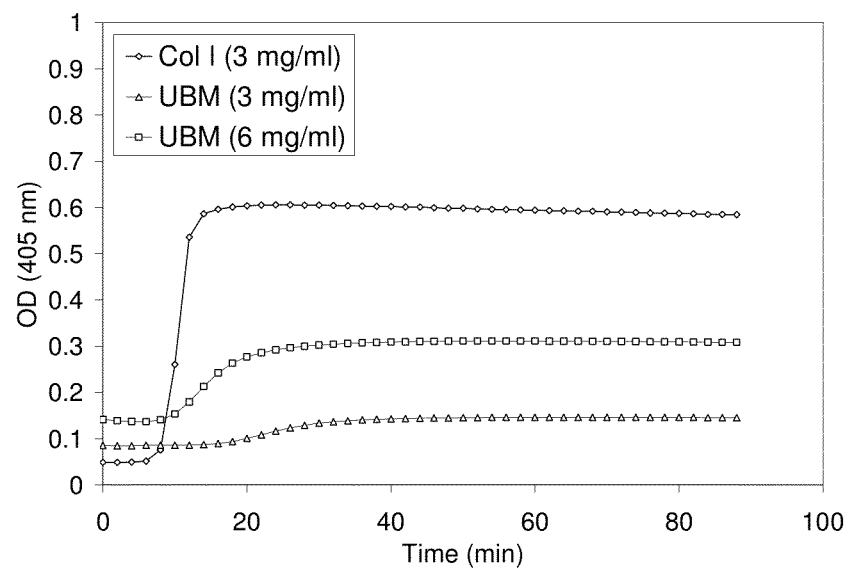
FIG. 8A shows turbidimetric gelation kinetics of Col I gels and UBM gels, which was determined spectrophotometrically by measuring absorbance during gelation. Results are shown for measured absorbance values.
Figure 8B:
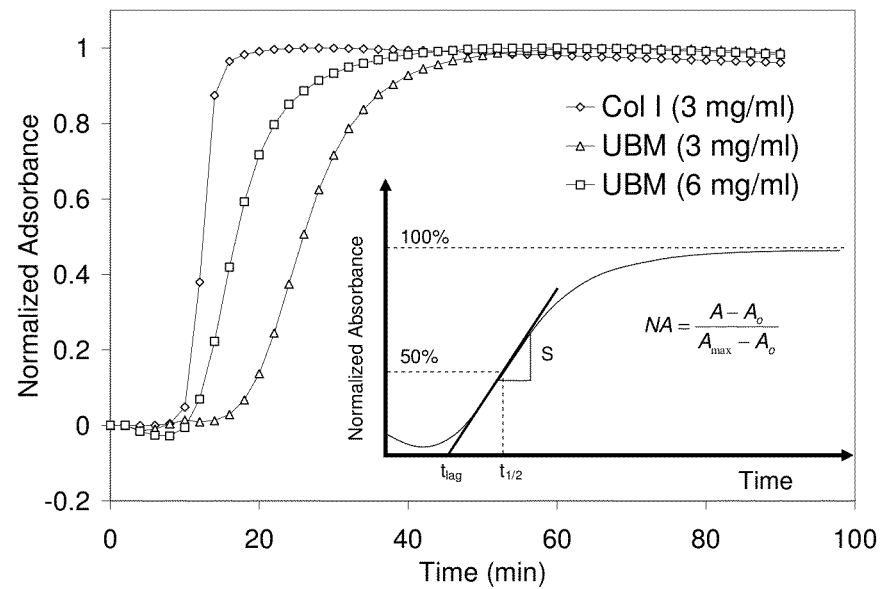
FIG. 8B shows turbidimetric gelation kinetics of Col I gels and UBM gels, which was determined spectrophotometrically by measuring absorbance during gelation. Results are shown for normalized absorbance values, which allows for calculating kinetic parameters such as t1/2 (time to reach 50% of maximum turbidity), tlag (lag time of gelation) and S (speed of gelation).
Figure 9:
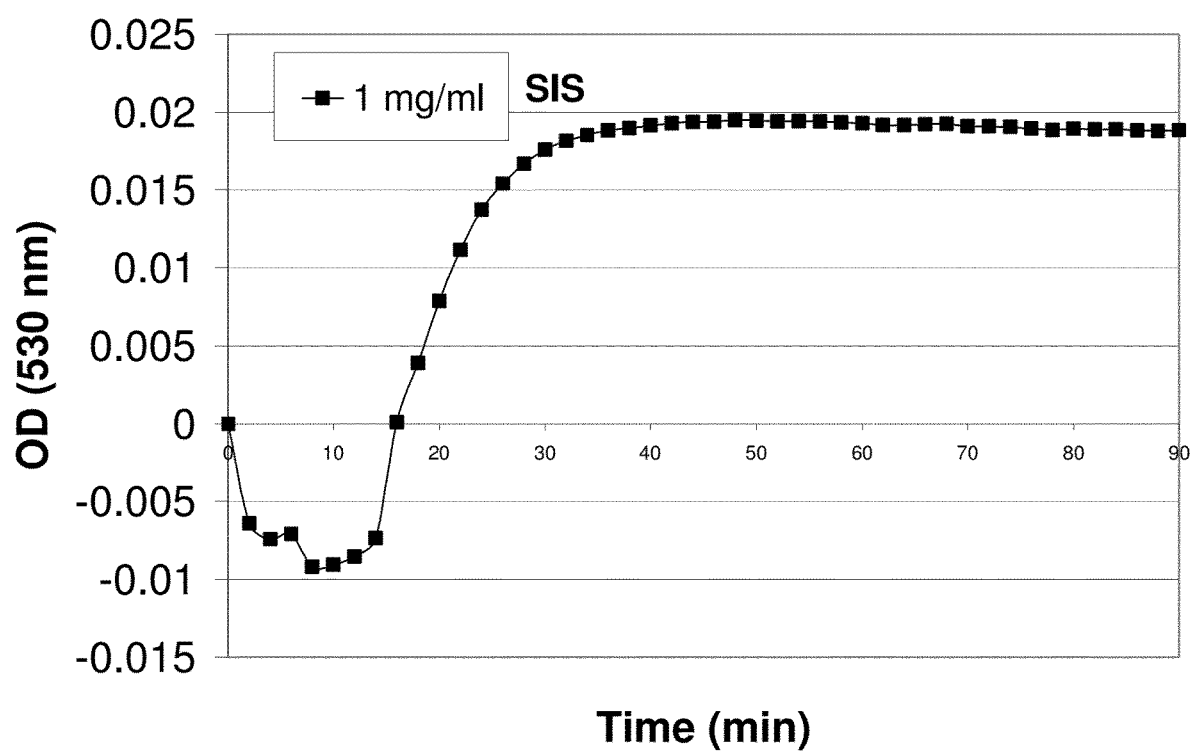
FIG. 9 shows turbidimetric gelation kinetics of 1 mg/mL small intestine submucosa (SIS) gels.

Turbidimetric gelation kinetics was determined spectrophotometrically as previously described (Gelman R A, et al., "Collagen fibril formation. Evidence for a multistep process," (1979) J. Biol. Chem. 254(1):180-6). Final pre-gel solutions at the appropriate concentration were kept at 4° C. and transferred to a cold 96 well plate by placing 100 μl per well in triplicates. The SpectraMax spectrophotometer (Molecular Devices) was pre-heated to 37° C., the plate was placed in the spectrophotometer, and the turbidity of each well was measured at 405 nm every 2 minutes for 1.5 hours (FIG. 8A). Turbidity can also be measured at 530 nm (FIG. 9). The absorbance values were recorded and normalized as shown in FIG. 8B. The time needed to reach 50% of the maximum turbidity measurement (e.g. maximum absorbance value) was defined as $t_{1/2}$ and the lag phase ($t_{lag}$) was calculated by extrapolating the linear growth of the curve. The speed (S) of the gelation based on turbidimetric measurements was determined by calculating the slope of the growth portion of the curve as shown in FIG. 8B.

Dynamic oscillatory measurements are commonly used in fundamental studies of gelation and in characterizing the viscoelastic properties of gels. The sample was subjected to an oscillatory strain of:

$$\gamma(0) = \gamma_0 \cos(2\pi ft) \quad (1)$$

where $\gamma_0$ was the amplitude of the sinusoidal strain, t was the time, and f was the frequency. The sample developed a sinusoidal stress described as follows:

$$\sigma(t) = |G^*|\gamma(t) \quad (2)$$

where $G^*$ was the frequency dependent complex modulus of the sample. The real part of $G^*$, denoted G', was in phase with the applied strain and was called the storage modulus since it corresponded to storage of mechanical energy in the elastic deformation of the sample. The imaginary portion of $G^*$, denoted G", was 90° out of phase with the applied strain and was called the loss modulus since it corresponded to the loss of energy by viscous dissipation within the sample. Since the sample was expected to develop solid-like characteristics as gelation proceeds, G' was expected to increase significantly.

A final property of interest was the magnitude of the complex viscosity defined as follows:

$$|\eta^*| = \frac{|G^*|}{2\pi f} = \frac{\sqrt{G'^2 + G''^2}}{2\pi f} \quad (3)$$

where $|\eta^*|$ was the frequency dependent complex viscosity, $G^*$ was the frequency dependent complex modulus, and f was the frequency. It is common to fit complex viscosity versus frequency data to a power-law of the form:

$$|\eta^*| = kf^n \quad (4)$$

where k and n are both constants.

Rheological experiments were performed with a TA Instruments AR2000 stress-controlled rheometer using a 40 mm-diameter parallel plate geometry and a Peltier cell to maintain the sample temperature. The samples were prepared as discussed earlier and loaded into the rheometer with the Peltier cell maintaining a temperature of 15° C. The sample edge was protected from evaporation by applying mineral oil. The viscosity of the sample was first measured by applying a constant stress of 1 Pa on the sample for one minute at 15° C. The temperature was then set to 37° C. to induce gelation; the Peltier cell typically reached a temperature of 30° C. within 10 seconds and 37° C. within 50 seconds. During this increase in temperature and the subsequent gelation, the oscillatory moduli of the sample were monitored continuously at a fixed frequency of 0.159 Hz (1 rad/s) and a strain of 5%. When there was no further change in the elastic modulus (G') with time, gelation was deemed to be complete. The final linear viscoelastic properties of the gel were measured by performing a frequency sweep between 15.9 Hz and 0.08 Hz at 37° C. and 5% strain and fitted to equation 4.

The turbidimetric gelation kinetics and the calculated parameters are shown in FIG. 8 and the results presented in Table 1. The turbidimetric gelation kinetics for UBM and collagen type I gels followed a sigmoidal shape (FIG. 8A). Collagen type I gels at a concentration of 3 mg/ml became more turbid following gelation than UBM-gel at a concentration of 3 mg/ml and 6 mg/ml (FIG. 8A). The lag phase ($t_{lag}$) and the time required to reach half the final turbidity ($t_{1/2}$) were greater in the UBM gel (at 3 and 6 mg/ml) than collagen type I (3 mg/ml). In addition, the speed of the turbidimetric gelation kinetics (S) was lower for UBM when compared to collagen type I. There was no change in $t_{lag}$, $t_{1/2}$, and S in UBM gels with a change in concentration but there was a change in the maximum turbidity reached.

Turbidimetric kinetics of 1 mg/mL SIS gel also followed a sigmoidal shape (FIG. 9). Whereas UBM measurements were obtained at 405 nm, SIS measurements were obtained at 530 nm. SIS measurements also displayed a decrease in turbidity before maximum turbidity was reached.

Figure 10:
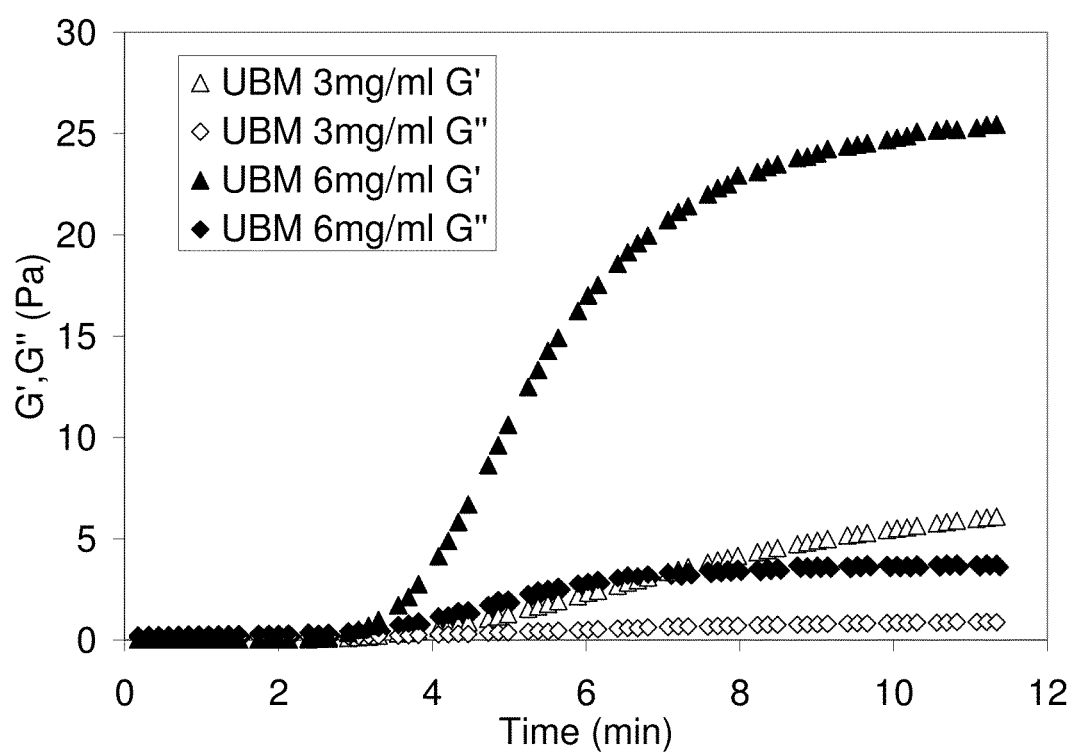
FIG. 10 shows rheological measurements during the gelation of UBM gels, where gelation was determined mechanically by monitoring the oscillatory moduli of the sample at a fixed frequency during gelation. Results are shown of the elastic modulus (G') and of the viscosity modulus (G") for 3 mg/ml UBM gel and for 6 mg/ml UBM gel.
Figure 12:
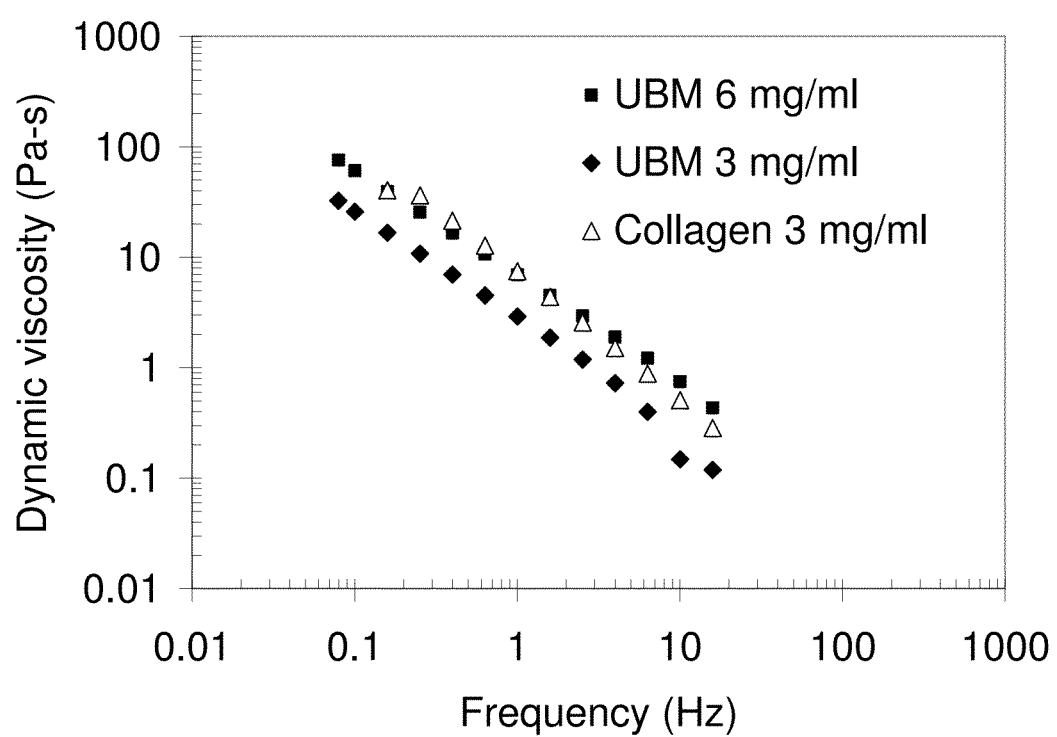
FIG. 12 shows the effect of frequency on the dynamic viscosity of 3 mg/ml Col I gel, 3 mg/ml UBM gel and 6 mg/ml UBM gel.

Both the storage modulus (G') and the loss modulus (G") of UBM gels changed over time with a sigmoidal shape after the temperature of the sample was raised from 15° C. to 37° C. (FIG. 10). G' and G" reached a steady state after approximately 8 minutes, suggesting that gelation had occurred. The kinetics of G' and G" were faster than the turbidimetric kinetics. The viscosities of both UBM and collagen type I are shown in FIG. 12 over a frequency range of ~0.08-15 Hz and the results are summarized in Table 1.

Figure 11A:
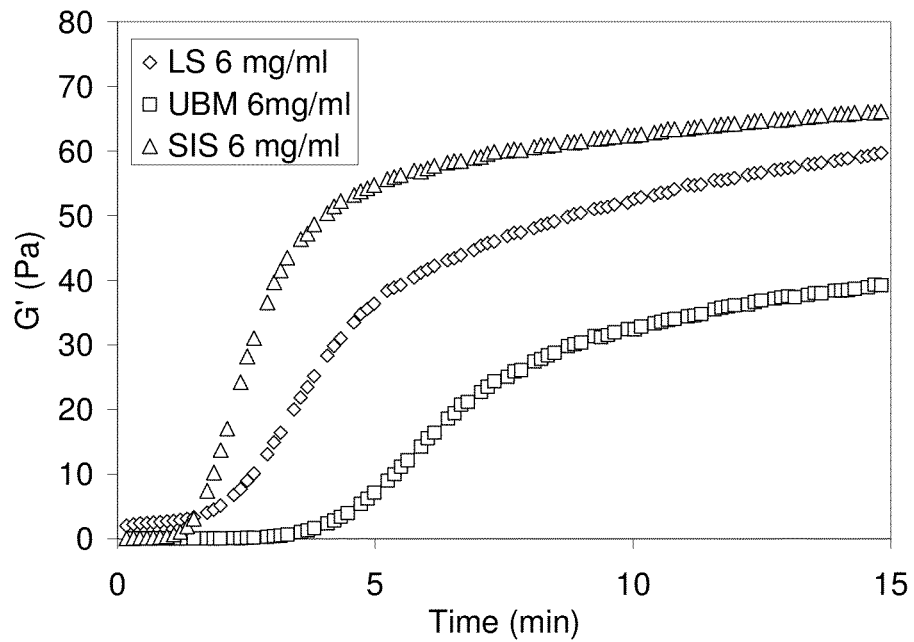
FIG. 11A shows rheological measurements during the gelation of LS (liver stroma) and SIS gels. Gelation kinetics was determined at 5% strain and 1 rad/sec. Results show the elastic modulus (G') for LS, SIS and UBM gels at 6 mg/mL.
Figure 11B:
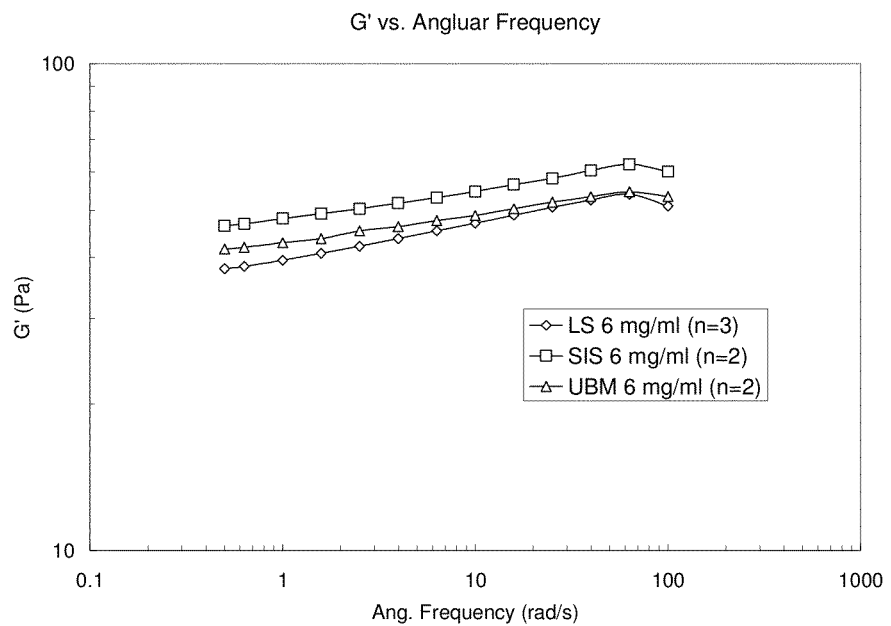
FIG. 11B shows rheological measurements during the gelation of LS (liver stroma) and SIS gels. Gelation kinetics was determined at 5% strain and 1 rad/sec. Results show the storage modulus (G') as a function of angular frequency was also determined for LS, UBM and SIS gels at 6 mg/ml.

The storage modulus (G') of LS and SIS gels also changed over time with a sigmoidal shape after the temperature of the sample was raised to 37° C. (FIG. 11A). Kinetics of G' for both LS and SIS gels were faster than kinetics of G' for UBM gels. The storage modulus (G') of LS, SIS and UBM gels were also measured as a function of angular frequency (FIG. 11B).

TABLE 1

Results from the turbidimetric analysis of the UBM gelation kinetics. Data represents mean ± SD. Three samples were tested (n = 3).

| Material | k | $t_{1/2}$ | $t_{lag}$ |
|---|---|---|---|
| Collagen type I 3 mg/ml | 0.20 (0.01)* | 12.2 (1.1)* | 9.7 (0.8)* |
| UBM 3 mg/ml | 0.07 (0.01) | 24.4 (2.4) | 15.8 (2.0) |
| UBM 6 mg/ml | 0.09 (0.04) | 22.4 (4.9) | 14.1 (3.7) |

*$p < 0.05$

In an effort to explore the feasibility of using UBM as an injectable material, multiple trials were performed to test them in an injection setting. ECM powder suspended in saline and UBM gels were tested side by side to see if they could successfully pass through injection needles frequently used in medical procedures such as vocal cord augmentation. These needles had 1 cm long, 25 gauge caliber tips that are attached to 25 cm long, 16 gauge needle shafts. UBM gels easily and consistently passed through these needles. The UBM powder suspension had an upper limit concentration of 10 mg/ml above which the needle would be frequently occluded, making it difficult to determine the actual amount of ECM delivered. This trial showed the feasibility of using the UMB gel as an injectable material (Table 2).

TABLE 2

Comparison of the viscosity of UBM gels with injectable materials commercially available.

| Material | k | n | $r^2$ | Frequency Range [Hz] | REF |
|---|---|---|---|---|---|
| Urinary Bladder Matrix 3 mg/ml | 2.35 | −1.0617 | 0.988 | 0.01-15 | — |
| Urinary Bladder Matrix 6 mg/ml | 5.69 | −0.9547 | 0.999 | 0.01-15 | — |
| Gelatin (Gelfoam) | 149.39 | −0.9030 | 0.997 | 0.01-15 | Chan et al. [a] |
| Zyplast ™ | 99.851 | −0.9145 | 0.998 | 0.01-15 | Chan et al. [a] |
| Zyderm ™ | 66.395 | −0.9154 | 0.998 | 0.01-15 | Chan et al. [a] |
| Zyderm ™ | 12 | −0.860 | 0.977 | 0.01-100 | Klemuk et al. [b] |
| Cymetra ® | 19.9 | −0.778 | 0.972 | 0.01-100 | Klemuk et al. [b] |
| Hyaluronic Acid-DTPH | 3.19 | −0.744 | 0.974 | 0.01-100 | Klemuk et al. [b] |
| Human abdominal subcutaneous fat | 23.576 | −0.9508 | 0.994 | 0.01-15 | Chan et al. [a] |
| Polytetra-fluoroethylene (PTFE) | 1151.9 | −1.0267 | 0.997 | 0.01-15 | Chan et al. [a] |

[a] Chan R W, et al. Viscosities of implantable biomaterials in vocal fold augmentation surgery. *Laryngoscope.* 1998 May; 108(5): 725-31.
[b] Klemuk S A, et al. Viscoelastic properties of three vocal-fold injectable biomaterials at low audio frequencies. *Laryngoscope.* 2004 September; 114(9): 1597-603.

Example 14—Hybrid Inorganic/ECM Scaffold

Restoration of joint kinematics after limb amputation and replacement with a prosthesis is limited due to the inability to attach existing musculature to the prosthesis via boney insertion of tendons (Higuera, C. A., et al., *J Orthop Res.* 1091-9 (23) 2005). Although a variety of porous titanium and tantalum alloys have been successful at promoting bone ingrowth, there are no alternatives to promote the ingrowth of fibrocartilaginous tissue that restores a ligament or tendon insertion site. Recently, porous tantalum scaffolds have been investigated for their ability to promote ingrowth of a vascularized fibrous tissue with promising mechanical strength (Hacking, S. A., et al.: *J Biomed Mater Res,* 631-8 (52) 2000). Naturally derived extracellular matrix (ECM) scaffolds from the porcine small intestine and urinary bladder (UBM) have also been shown to form well organized tendon, ligament, cartilage, and bone, as well as strong boney insertion sites with good mechanical strength (Badylak, S. F.: *Transpl Immunol.* 367-77 (12) 2004; Dejardin, L. M., et al.: *AJSM.* 175-84 (29) 2001). It is reasonable to expect that a porous tantalum or titanium scaffold with an ECM embedded within the pores may improve the ingrowth of soft tissue into the metal surface and promote the formation of fibrocartilaginous tissue. The goal of the current study was to determine the feasibility of coating a porous titanium scaffold with an ECM gel for the eventual application of ligament or tendon insertion repair.

UBM powder was produced as described previously (Freytes, D O et al, *Biomaterials*, 2004. 25(12): 2353-61). A UBM gel digest was prepared by mixing one gram of lyophilized UBM powder with 100 mg of pepsin in 100 mL of 0.01 M HCl under constant stirring for ~48 hrs at room temperature. UBM gel polymerization was initiated by bringing the pH and the ionic strength to physiological range using PBS at 37° C. Complete polymerization of the gel occurred within 30 min. The porous metal scaffolds were cleaned with acetone, methanol, and water, and passivated with 20-45% nitric acid.

The contact angles between the UBM gel digest (before [10 mg/ml] and after physiologic activation [6 mg/ml]) and sheets of CP Ti or Ti 6Al 4V were measured. One ml of the digest was added to each surface and a digital photograph was taken for subsequent angle determination.

Two methods tested for ability to promote penetration of the polymerized UBM gel into either CP titanium fiber mesh or CP titanium sintered beads. The entire surface of each porous metal scaffold was covered with activated UBM gel for 5 minutes. For half of the scaffolds, the gel was permitted to penetrate under static conditions, while in the other half of the samples penetration took place using ultrasonication. Dye was added to visualize the gel.

To verify the presence of UBM gel within the porous titanium scaffolds and to better understand the interaction between the UBM gel and the metal, specimens were prepared for environmental scanning electron microscopy (ESEM). Since the samples were able to be visualized with ESEM while still in the hydrated condition, the interactions between the titanium scaffold and the UBM gel were able to be determined without disruption of the ECM by dehydration.

Figure 13A:
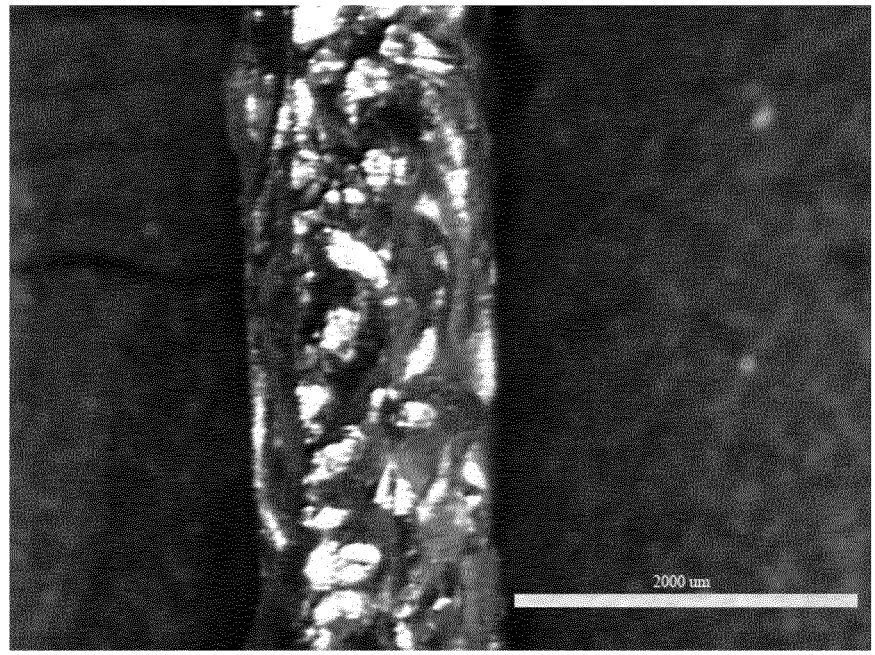
FIG. 13A shows a digital photograph of a porous titanium fiber penetrated with UBM gel, where the fiber was treated without ultrasonication. Scale bars are 2000 µm.
Figure 13B:
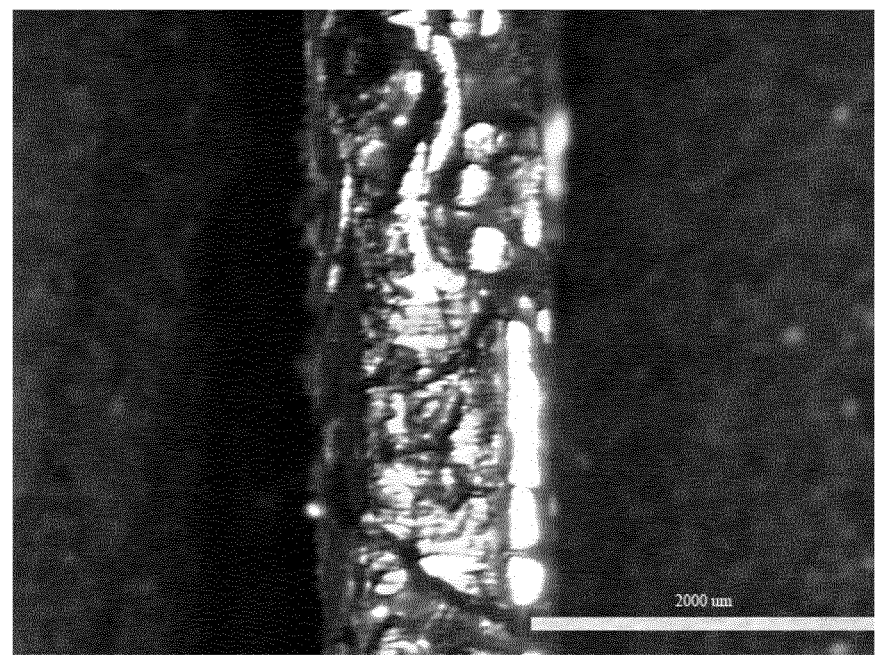
FIG. 13B shows a digital photograph of a porous titanium fiber penetrated with UBM gel, where the fiber was treated with ultrasonication. Scale bars are 2000 µm.
Figure 14A:
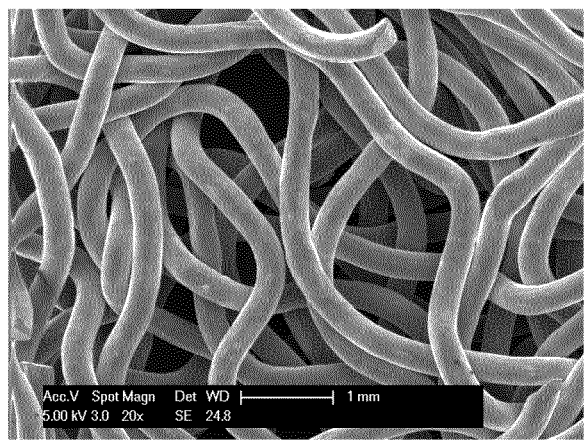
FIG. 14A shows an SEM image of a porous metal scaffold containing Ti6Al4V wires in a fiber mesh.
Figure 14B:
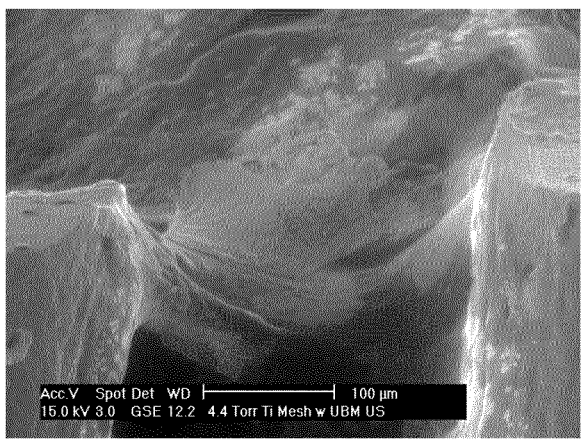
FIG. 14B shows an ESEM image of the hybrid ECM/porous metal scaffold, where UBM gel coats both the Ti6Al4V wires.
Figure 14C:
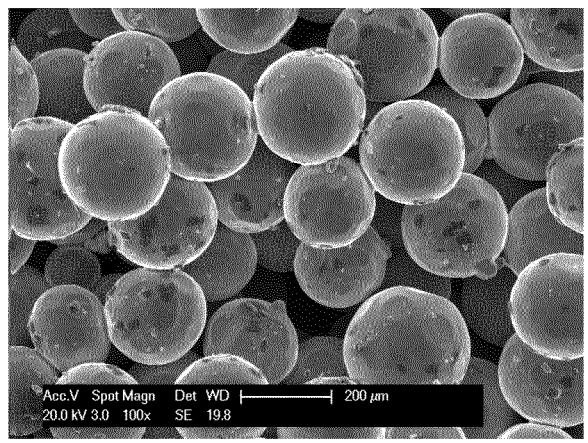
FIG. 14C shows an SEM image a porous metal scaffold containing sintered commercially pure titanium (CP Ti) beads.
Figure 14D:
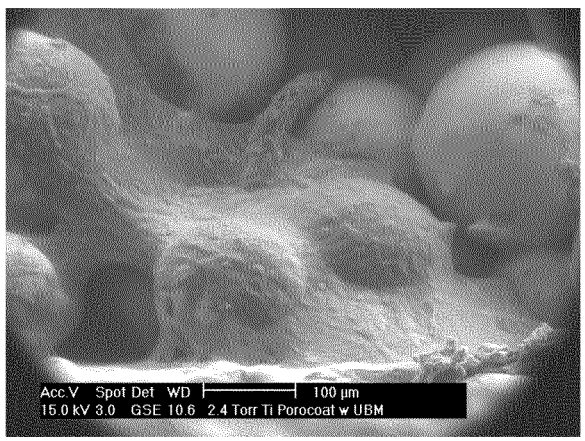
FIG. 14D shows an ESEM image of the hybrid ECM/porous metal scaffold and the CP Ti beads after exposure to ultrasonication.

Both the UBM gel digest and the activated UBM gel wet the surface of the CP Ti and Ti 6Al 4V well (Table 4). Therefore, the porous metal should not exclude the ECM. Based on these results, subsequent experiments focused on the activated gel. The UBM gel was able to penetrate half way through the thickness of each porous metal scaffold in the static condition. With the addition of ultrasonication, pores were infiltrated through the entire thickness of the scaffold (FIGS. 13A and 13B). Examination of the hybrid scaffolds with ESEM showed excellent penetration within and coverage of the porous titanium (FIGS. 14A-14D).

It is possible to create a hybrid ECM/porous metal scaffold using UBM gel and a porous titanium scaffold. Future studies will evaluate whether these scaffolds can support cell growth in vitro and promote connective tissue ingrowth in vivo. The eventual goal of this effort is to develop a scaffold that will promote ingrowth of soft tissue into the metal to serve as an insertion site for ligaments and tendons.

TABLE 4

Contact angle for UBM material on titanium alloys (Mean ± SD)

| Type of Metal | UBM digest | UBM gel |
|---|---|---|
| CP Ti | 46.8 ± 1.3 | 27.0 ± 4.0 |
| Ti6Al4V | 38.2 ± 4.8 | 41.3 ± 1.6 |

Example 15—Sterilization of Pre-Digest ECM Materials

Figure 15:
FIG. 15 shows a qualitative observation of hydrogel formation following terminal sterilization. Compared to the non-sterilized controls, the ability of dermal ECM to form a hydrogel following terminal sterilization was abolished after the metallic ring molds (top image) were removed.
Figures 16A, 16B, 16C, 16D:
FIG. 16A shows non-sterilized lyophilized pre-gel.
FIG. 16B shows non-sterilized lyophilized pre-gel reconstituted in HCl
FIG. 16C shows non-sterilized lyophilized pre-gel reconstituted in deionized water.
FIG. 16D shows lyophilized pre-gel sterilized with EtO and reconstituted either in water or HCl. Comparison of FIG. 16B-C shows that reconstitution was complete for all samples except those after sterilization in HCl (FIG. 16D).

It has been noted that terminal sterilization of an ECM scaffold inhibits subsequent hydrogel formation of protease-solubilized ECM materials. The following illustrates the effect of sterilization on qualitative hydrogel formation, using dermal ECM that has not been dialyzed (that is, intact ECM as described above). Porcine dermis was decellularized essentially as described above, and subjected to various methods of terminal sterilization. The dermal ECM sheets were terminally sterilized by exposure to (1) gamma radiation at a dosage of 10 kGy, 25 kGy, and 40 kGy, (2) electron beam radiation at a dosage of 10 kGy, 25 kGy, and 40 kGy, and (3) ethylene oxide (EtO) gas at a dose of 750 mg/h for 16 h. Control dermal ECM sheets were not sterilized. The sterilized and control dermal ECM was then mechanically comminuted in a Wiley Mill with a 60 mesh sieve, enzymatically digested for 48 hours at 4° C. in 1 mg/ml pepsin in a solution of 0.01 N HCl to produce a pre-gel, and tested for hydrogel formation by neutralization to approximately pH 7.4 at room temperature (20-25° C.) and then raising the temperature to 37° C. in an incubator without $CO_2$. FIG. 15 shows the terminally sterilized dermal ECM were unable to form a hydrogel regardless of sterilization method whereas the non-sterilized dermal ECM formed a solid gel and maintained form after removal of metallic ring molds.

Example 16—Sterilization of Lyophilized Product

Due to the ineffective hydrogel formation after terminal sterilization of the pre-digest decellularized ECM material, and recognizing the clinical/commercial need for sterilization, we hypothesized that changing the form of material prior to sterilization would allow for ECM gelation. Instead of the lyophilized solid ECM sheets, we sterilized a lyophilized pre-gel prepared from non-dialyzed (intact ECM as described above), mechanically comminuted ECM that is enzymatically digested essentially as described above) and tested whether hydrogel formation would occur. ECM derived from small intestinal submucosa (SIS-ECM) was decellularized according to a standard protocol without dialysis. The SIS-ECM powder was enzymatically digested in the same manner as above, frozen at −80 C on dry ice, and lyophilized. The lyophilized pre-gel was then sterilized by exposure to EtO gas at a dose of 750 mg/h for 16 h and/or reconstituted in deionized water or 0.01N HCl (FIGS. 16A-16D). FIGS. 16A-16D show complete reconstitution at room temperature using water and HCl prior to sterilization but after sterilization (FIG. 16D) only pre-gel in deionized water was completely reconstituted.

Figure 17:
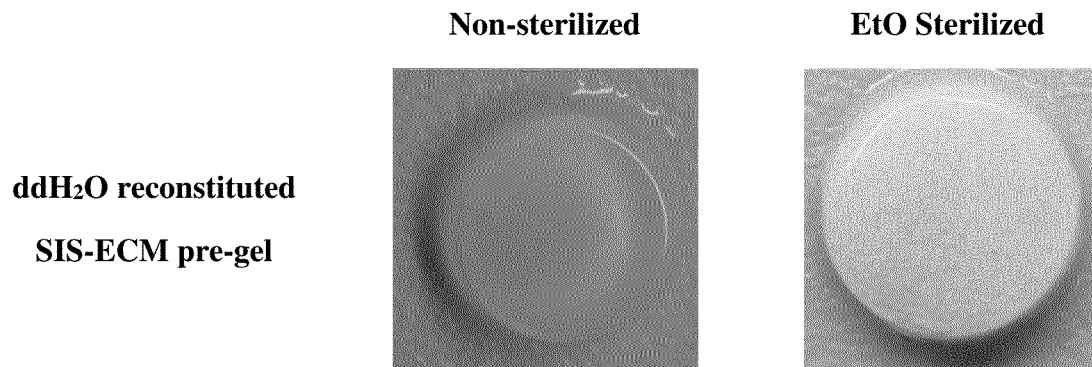
FIG. 17 shows sterilization of lyophilized SIS-ECM pre-gel results in hydrogel formation.

Since only pre-gel in deionized water was completely reconstituted, these samples were tested for hydrogel formation. FIG. 17 shows that both non-sterilized and EtO sterilized pre-gel resulted in a solid gel when neutralized and placed in a 37° C. incubator without $CO_2$, which maintained form after removal of metallic ring molds.

Figure 18:
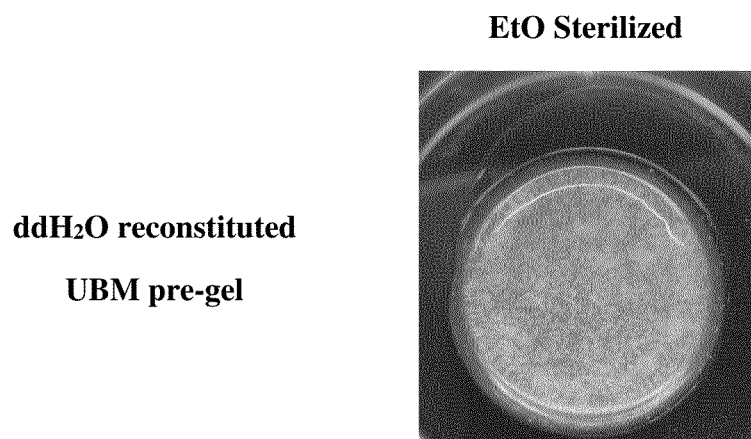
FIG. 18 shows sterilization of lyophilized UBM pre-gel results in hydrogel formation.

To corroborate the results shown in FIG. 17, ECM derived from urinary bladder (UBM) was decellularized according to a standard protocol and tested in the same manner as the SIS-ECM, above. The results similarly showed that sterilization of the lyophilized pre-gel was conducive to hydrogel formation (FIG. 18).

Example 17—Sterilization of Lyophilized Product—Further Studies

Expanding the work of the Examples above, ECM materials, prepared essentially as described above, are sterilized in different forms, as follows: ECM material that is not digested, both in powder and 2D sheet form; hydrated powder or 2D sheet ECM material that is not digested;

pre-gel solution that is acid-protease digested, but not neutralized; and/or lyophilized pre-gel that is digested, but not neutralized. ECM material from various sources are tested, including urinary bladder, spleen, liver, heart, pancreas, ovary, small intestine, central nervous system (CNS), adipose tissue, and/or bone.

The materials are sterilized by ethylene oxide, gamma radiation (2 kGy, 30 kGy @ ambient and −80 C), electron beam radiation (2 kGy, 30 kGy @ ambient and −80 C), and/or supercritical $CO_2$ (low and/or high). A non-sterilized control also is run.

Figure 19A:
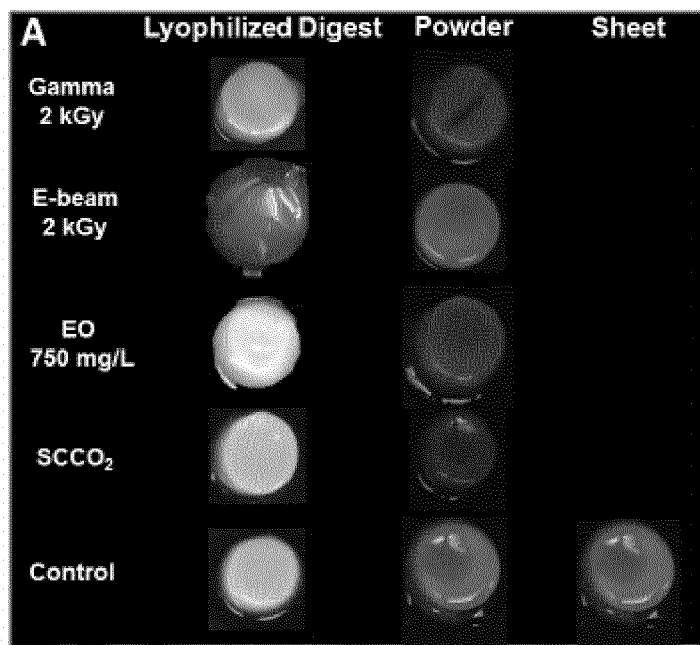
FIG. 19A is a comparison of various sterilization methods of decellularized UBM.
Figure 19B:
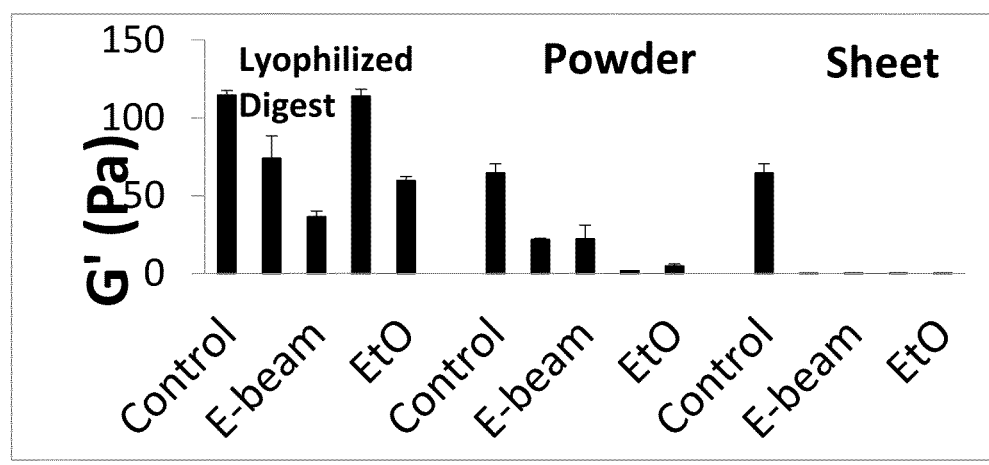
FIG. 19B is a qualitative comparison of FIG. 19A.

Example 18—Decellularized Urinary Bladder Matrix (UBM) Subjected to Various Sterilization Methods Urinary bladder matrix was decellularized according to a standard protocol and subjected to various sterilization methods. Hydrogel formation was tested following sterilization of (1) the UBM sheet, (2) mechanically comminuted UBM powder, and (3) following digestion and lyophilization. Each gel was formed in a ring mold and imaged (FIG. 19A). Hydrogel formation was then tested with the most rigid hydrogels formed by the lyophilized digests, followed by the powder form, as shown by the storage modulus values (see FIG. 19B). Sterilization of the UBM sheet did not allow for subsequent hydrogel formation. Each sterilization method has an impact upon hydrogel formation but this can be mitigated by the starting form of the ECM material, most clearly evidenced by a comparison of the storage moduli of the $scCO_2$ and EtO lyophilized digest versus powder forms. Interestingly, the non-sterilized control samples also show a distinct difference in hydrogel formation with the lyophilized digest forming a more rigid gel. Qualitatively, the lyophilized digest formed the most rigid hydrogel followed by powder while sterilization of the UBM sheet did not allow for subsequent hydrogel formation. The qualitative trends in gel rigidity were corroborated by rheological characterization of the gel stiffness (i.e., storage modulus or G'). Together, these figures highlight the importance of the form of ECM (i.e., sheet, powder, or digest) that is exposed to sterilization.

The present invention has been described in accordance with several examples, which are intended to be illustrative, rather than limiting, in all aspects. Thus, the present invention is capable of many variations in detailed implementation, which may be derived from the description contained herein by a person of ordinary skill in the art, and should not be limited by the preceding description, but should be construed to be as broad in scope as the following claims.

We claim:

1. A gellable extracellular matrix (ECM) composition comprising a decellularized, enzymatically digested, dried, terminally sterilized, intact extracellular matrix, wherein said composition is capable of forming a gel upon hydration, neutralization to pH 7.2-7.8, and warming to a temperature greater than 25° C.

2. The composition of claim 1, wherein the composition further comprises a protease.

3. The composition of claim 2, wherein the protease is pepsin or trypsin.

4. The composition of claim 1, wherein the extracellular matrix is bioactive.

5. The composition of claim 1, wherein the extracellular matrix is derived from urinary bladder, spleen, liver, heart, pancreases, ovary, small intestine, large intestine, colon, esophagus, central nervous system tissue, adipose tissue, dermis, or bone.

6. The composition of claim 1, wherein the extracellular matrix is from a human, monkey, pig, cow, or sheep.

7. The composition of claim 1, wherein the warming is to a temperature of 37° C.

8. A terminally sterilized extracellular matrix (ECM) digest solution comprising a hydrated, decellularized, enzymatically digested, terminally sterilized, intact extracellular matrix, wherein said digest solution is capable of forming a gel upon neutralization to pH 7.2-7.8 and warming to a temperature greater than 25° C.

9. The digest solution of claim 8, wherein the solution further comprises a protease.

10. The digest solution of claim 9, wherein the protease is pepsin or trypsin.

11. The digest solution of claim 8, wherein the extracellular matrix is bioactive.

12. The digest solution of claim 8, wherein the extracellular matrix is derived from urinary bladder, spleen, liver, heart, pancreases, ovary, small intestine, large intestine, colon, esophagus, central nervous system tissue, adipose tissue, dermis, or bone.

13. The digest solution of claim 8, wherein the extracellular matrix is from a human, monkey, pig, cow, or sheep.

14. A terminally sterilized extracellular matrix (ECM) digest solution comprising a hydrated, decellularized, enzymatically digested, terminally sterilized, intact extracellular matrix, wherein said digest solution has a pH 7.2-7.8 and forms a gel when warmed to a temperature greater than 25° C.

15. The digest solution of claim 14, wherein the digest solution forms a gel when warmed to 37° C.

16. The digest solution of claim 14, wherein the extracellular matrix is bioactive.

17. The digest solution of claim 14, wherein the extracellular matrix is derived from urinary bladder, spleen, liver, heart, pancreases, ovary, small intestine, large intestine, colon, esophagus, central nervous system tissue, adipose tissue, dermis, or bone.

18. The digest solution of claim 14, wherein the extracellular matrix is from a human, monkey, pig, cow, or sheep.

* * * * *